(12) United States Patent
Jodaitis et al.

(10) Patent No.: US 10,188,528 B2
(45) Date of Patent: Jan. 29, 2019

(54) INTERVETERBRAL DISC PROSTHESIS INSERTION ASSEMBLIES

(71) Applicant: LDR Medical, Rosières Près Troyes (FR)

(72) Inventors: Alexandre Jodaitis, Morlanwelz (BE); Herve Dinville, St-Parres-Aux-Tertres (FR); Alexis Mercier, Troyes (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 14/242,177

(22) Filed: Apr. 1, 2014

(65) Prior Publication Data

US 2014/0214168 A1 Jul. 31, 2014

Related U.S. Application Data

(63) Continuation of application No. 12/527,373, filed as application No. PCT/IB2008/000349 on Feb. 15, (Continued)

(51) Int. Cl.
*A61F 2/44* (2006.01)
*A61F 2/46* (2006.01)
(Continued)

(52) U.S. Cl.
CPC .......... *A61F 2/4611* (2013.01); *A61F 2/0095* (2013.01); *A61F 2/442* (2013.01); (Continued)

(58) Field of Classification Search
CPC ...................... A61F 2/44–2/447; A61F 2/4611
(Continued)

(56) References Cited

U.S. PATENT DOCUMENTS 1,436,573 A 11/1922 Choppinet et al.
2,836,442 A 5/1958 Moskovitz
(Continued)

FOREIGN PATENT DOCUMENTS

AU 2008215916 A1 8/2008
CA 2472708 A1 2/2005
(Continued)

OTHER PUBLICATIONS

U.S. Appl. No. 10/498,234, filed May 19, 2005, Beaurain, Jacques, et al.
(Continued)

*Primary Examiner* — Jan Christopher Merene
*Assistant Examiner* — Steven Cotroneo
(74) *Attorney, Agent, or Firm* — Schwegman Lundberg & Woessner, P.A.

(57) ABSTRACT

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various other embodiments, the prosthesis and an insertion tool are provided in a sterile pack, with the prosthesis components and the insertion tool sterilized and packaged in one or more types or layers of sterile packaging.

20 Claims, 20 Drawing Sheets

Related U.S. Application Data 2008, now Pat. No. 8,685,100, which is a continuation-in-part of application No. 11/676,237, filed on Feb. 16, 2007, now Pat. No. 8,465,546.

(51) Int. Cl.
  *A61F 2/00* (2006.01)
  *A61F 2/30* (2006.01)

(52) U.S. Cl.
  CPC ........ *A61F 2/4425* (2013.01); *A61F 2/30767* (2013.01); *A61F 2002/3071* (2013.01); *A61F 2002/30607* (2013.01); *A61F 2002/30616* (2013.01); *A61F 2002/30617* (2013.01); *A61F 2002/30662* (2013.01); *A61F 2002/30711* (2013.01); *A61F 2002/30714* (2013.01); *A61F 2002/30904* (2013.01); *A61F 2002/443* (2013.01); *A61F 2002/4622* (2013.01); *A61F 2002/4627* (2013.01); *A61F 2002/4628* (2013.01); *A61F 2002/4681* (2013.01); *A61F 2250/0062* (2013.01); *A61F 2250/0085* (2013.01); *A61F 2250/0086* (2013.01); *A61F 2250/0089* (2013.01); *A61F 2250/0097* (2013.01)

(58) Field of Classification Search
  USPC ................. 606/86 A, 99; 623/17.11–17.16
  See application file for complete search history.

(56) References Cited

U.S. PATENT DOCUMENTS

| | | |
|---|---|---|
| 3,325,197 A | 6/1967 | Wehner |
| 3,374,786 A | 3/1968 | Callender, Jr. |
| 3,486,505 A | 12/1969 | Morrison |
| 3,791,380 A | 2/1974 | Dawidowski |
| 3,857,642 A | 12/1974 | Miller |
| 3,892,232 A | 7/1975 | Neufeld |
| 3,958,278 A | 5/1976 | Lee et al. |
| 4,009,712 A | 3/1977 | Burstein et al. |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland et al. |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,655,778 A | 4/1987 | Koeneman |
| 4,657,001 A | 4/1987 | Fixel |
| 4,664,305 A | 5/1987 | Blake, III et al. |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A | 7/1988 | Buettner-Janz et al. |
| 4,759,769 A | 7/1988 | Hedman et al. |
| 4,787,378 A | 11/1988 | Sodhi |
| 4,787,908 A | 11/1988 | Wyss et al. |
| 4,790,303 A | 12/1988 | Stefee |
| 4,791,918 A | 12/1988 | Von Hasselbach |
| 4,863,476 A | 9/1989 | Shepperd |
| 4,874,389 A | 10/1989 | Downey |
| 4,892,545 A | 1/1990 | Day et al. |
| 4,898,156 A | 2/1990 | Gatturna et al. |
| 4,911,718 A | 3/1990 | Lee et al. |
| 4,932,975 A | 6/1990 | Main et al. |
| 4,946,378 A | 8/1990 | Hirayama et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,071,437 A | 12/1991 | Steffee |
| 5,087,266 A | 2/1992 | Connell et al. |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,901 A | 7/1992 | Decoste |
| 5,171,281 A | 12/1992 | Parsons et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,234,447 A | 8/1993 | Kaster et al. |
| 5,242,448 A | 9/1993 | Pettine et al. |
| 5,246,458 A | 9/1993 | Graham |
| 5,258,009 A | 11/1993 | Conners |
| 5,258,031 A | 11/1993 | Salib et al. |
| 5,290,312 A | 3/1994 | Kojimoto |
| 5,300,074 A | 4/1994 | Frigg |
| 5,306,309 A * | 4/1994 | Wagner et al. ............ 623/17.16 |
| 5,314,477 A | 5/1994 | Marnay |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,397,364 A | 3/1995 | Kozak et al. |
| 5,401,269 A | 3/1995 | Buttner-janz et al. |
| 5,417,692 A | 5/1995 | Goble et al. |
| 5,417,712 A | 5/1995 | Whittaker et al. |
| 5,425,773 A | 6/1995 | Boyd et al. |
| 5,429,641 A | 7/1995 | Gotfried |
| 5,437,674 A | 8/1995 | Worcel |
| 5,443,514 A | 8/1995 | Steffee |
| 5,456,721 A | 10/1995 | Legrand |
| 5,458,601 A | 10/1995 | Young, Jr. et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,507,816 A | 4/1996 | Bullivant |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 566,360 A | 8/1996 | White |
| 5,545,229 A | 8/1996 | Parsons et al. |
| 5,549,617 A | 8/1996 | Green et al. |
| 5,554,191 A | 9/1996 | Lahille et al. |

(56) References Cited

U.S. PATENT DOCUMENTS

| | | |
|---|---|---|
| 5,556,431 A | 9/1996 | Buttner-janz |
| 5,562,689 A | 10/1996 | Green et al. |
| 5,562,738 A | 10/1996 | Boyd et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | Mcdevitt |
| 5,645,596 A | 7/1997 | Kim et al. |
| 5,655,698 A | 8/1997 | Yoon |
| 5,674,294 A | 10/1997 | Bainville et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,702,449 A | 12/1997 | Mckay |
| 5,702,450 A | 12/1997 | Bisserie |
| 5,702,472 A | 12/1997 | Huebner |
| 5,722,977 A | 3/1998 | Wilhelmy |
| 5,723,013 A | 3/1998 | Jeanson et al. |
| 5,741,253 A | 4/1998 | Michelson |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,807,403 A | 9/1998 | Beyar et al. |
| 5,824,094 A | 10/1998 | Serhan et al. |
| 5,827,328 A | 12/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,968,098 A | 10/1999 | Winslow |
| 5,980,522 A | 11/1999 | Koros et al. |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,088 A | 5/2000 | Winslow |
| 6,063,121 A | 5/2000 | Xavier et al. |
| 6,066,175 A | 5/2000 | Henderson et al. |
| 6,080,158 A | 6/2000 | Lin |
| 6,093,205 A | 7/2000 | Mcleod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,113,637 A | 9/2000 | Gill et al. |
| 6,113,638 A | 9/2000 | Williams et al. |
| 6,129,763 A | 10/2000 | Chauvin et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,214,050 B1 | 4/2001 | Huene |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,241,769 B1 | 6/2001 | Nicholson et al. |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson et al. |
| 6,277,149 B1 | 8/2001 | Boyle et al. |
| 6,283,998 B1 | 9/2001 | Eaton |
| 6,287,308 B1 | 9/2001 | Betz et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,319,257 B1 | 11/2001 | Carignan et al. |
| 6,342,074 B1 | 1/2002 | Simpson |
| 6,344,057 B1 | 2/2002 | Rabbe et al. |
| 6,364,880 B1 | 4/2002 | Michelson |
| 6,368,350 B1 | 4/2002 | Erickson et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,485,517 B1 | 11/2002 | Michelson |
| 6,500,205 B1 | 12/2002 | Michelson |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,753 B2 | 4/2003 | Cohen |
| 6,540,785 B1 | 4/2003 | Gill et al. |
| 6,558,423 B1 | 5/2003 | Michelson |
| 6,558,424 B2 | 5/2003 | Thalgott |
| 6,565,605 B2 | 5/2003 | Goble et al. |
| 6,572,653 B1 | 6/2003 | Simonson |
| 6,579,291 B1 | 6/2003 | Keith et al. |
| 6,579,320 B1 | 6/2003 | Gauchet et al. |
| 6,582,468 B1 | 6/2003 | Gauchet |
| 6,592,624 B1 | 7/2003 | Fraser et al. |
| 6,599,294 B2 | 7/2003 | Fuss et al. |
| 6,599,320 B1 | 7/2003 | Kuslich |
| 6,607,530 B1 | 8/2003 | Carl et al. |
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |

(56) References Cited

U.S. PATENT DOCUMENTS

| | | |
|---|---|---|
| 6,616,671 B2 | 9/2003 | Landry et al. |
| 6,636,071 B1 | 10/2003 | Yatabe |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,709,458 B2 | 3/2004 | Michelson |
| 6,716,247 B2 | 4/2004 | Michelson |
| 6,719,794 B2 | 4/2004 | Gerber et al. |
| 6,723,127 B2 | 4/2004 | Ralph et al. |
| 6,723,128 B2 | 4/2004 | Uk |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,749,636 B2 | 6/2004 | Michelson |
| 6,752,832 B2 | 6/2004 | Neumann |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,770,096 B2 | 8/2004 | Bolger et al. |
| 6,793,676 B2 | 9/2004 | Plouhar et al. |
| 6,793,679 B2 | 9/2004 | Michelson |
| 6,800,093 B2 | 10/2004 | Nicholson et al. |
| 6,805,714 B2 | 10/2004 | Sutcliffe |
| 6,808,537 B2 | 10/2004 | Michelson |
| 6,814,737 B2 | 11/2004 | Cauthen |
| 6,824,565 B2 | 11/2004 | Muhanna et al. |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,916,340 B2 | 7/2005 | Metzger et al. |
| 6,923,811 B1 | 8/2005 | Carl et al. |
| 6,923,830 B2 | 8/2005 | Michelson |
| 6,936,071 B1 | 8/2005 | Marnay et al. |
| 6,955,691 B2 | 10/2005 | Chae et al. |
| 6,962,606 B2 | 11/2005 | Michelson |
| 6,964,686 B2 | 11/2005 | Gordon |
| 6,966,929 B2 | 11/2005 | Mitchell |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,385 B2 | 2/2006 | Bonutti |
| 7,001,432 B2 | 2/2006 | Keller et al. |
| 7,008,453 B1 | 3/2006 | Michelson |
| 7,011,684 B2 | 3/2006 | Eckman |
| 7,025,787 B2 | 4/2006 | Bryan et al. |
| 7,033,394 B2 | 4/2006 | Michelson |
| 7,037,340 B2 | 5/2006 | Gau |
| 7,041,135 B2 | 5/2006 | Michelson |
| 7,041,136 B2 | 5/2006 | Goble et al. |
| 7,056,344 B2 | 6/2006 | Huppert et al. |
| 7,060,097 B2 | 6/2006 | Fraser et al. |
| 7,060,099 B2 | 6/2006 | Carli et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,105,023 B2 | 9/2006 | Eckman |
| 7,105,024 B2 | 9/2006 | Richelsoph |
| 7,112,206 B2 | 9/2006 | Michelson |
| 7,118,579 B2 | 10/2006 | Michelson |
| 7,118,580 B1 | 10/2006 | Beyersdorff et al. |
| 7,118,598 B2 | 10/2006 | Michelson |
| 7,128,760 B2 | 10/2006 | Michelson |
| 7,128,761 B2 | 10/2006 | Kuras et al. |
| 7,147,665 B1 | 12/2006 | Bryan et al. |
| 7,153,325 B2 | 12/2006 | Kim et al. |
| 7,163,561 B2 | 1/2007 | Michelson |
| 7,169,153 B2 | 1/2007 | Keller |
| 7,175,662 B2 | 2/2007 | Link et al. |
| 7,179,294 B2 | 2/2007 | Eisermann et al. |
| 7,198,644 B2 | 4/2007 | Schultz et al. |
| 7,204,851 B2 | 4/2007 | Trieu et al. |
| 7,204,852 B2 | 4/2007 | Marnay et al. |
| 7,211,112 B2 | 5/2007 | Baynham et al. |
| 7,217,291 B2 | 5/2007 | Zucherman et al. |
| 7,217,292 B2 * | 5/2007 | Ralph et al. ............... 623/17.16 |
| 7,217,293 B2 | 5/2007 | Branch |
| 7,223,289 B2 | 5/2007 | Trieu et al. |
| 7,232,463 B2 | 6/2007 | Falahee |
| 7,232,464 B2 | 6/2007 | Mathieu |
| 7,291,170 B2 | 11/2007 | Huppert |
| 7,326,248 B2 | 2/2008 | Michelson |
| 7,326,250 B2 | 2/2008 | Beaurain et al. |
| 7,404,795 B2 * | 7/2008 | Ralph et al. ................. 600/219 |
| 7,410,501 B2 | 8/2008 | Michelson |
| 7,419,505 B2 * | 9/2008 | Fleischmann et al. .... 623/17.11 |
| 7,431,735 B2 | 10/2008 | Liu et al. |
| 7,435,262 B2 | 10/2008 | Michelson |
| 7,442,209 B2 | 10/2008 | Michelson |
| 7,445,636 B2 | 10/2008 | Liu et al. |
| 7,445,635 B2 | 11/2008 | Fallin et al. |
| 7,455,692 B2 | 11/2008 | Michelson |
| 7,465,317 B2 | 12/2008 | Malberg et al. |
| 7,481,840 B2 | 1/2009 | Zucherman et al. |
| 7,494,507 B2 | 2/2009 | Dixon et al. |
| 7,494,508 B2 | 2/2009 | Zeegers |
| 7,503,933 B2 | 3/2009 | Michelson |
| 7,507,248 B2 | 3/2009 | Beaurain et al. |
| 7,517,363 B2 | 4/2009 | Rogers et al. |
| 7,540,882 B2 | 6/2009 | Michelson |
| 7,566,345 B1 | 7/2009 | Fallin et al. |
| 7,575,599 B2 | 8/2009 | Villiers et al. |
| 7,575,600 B2 | 8/2009 | Zucherman et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,608,107 B2 | 10/2009 | Michelson |
| 7,611,538 B2 | 11/2009 | Belliard et al. |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,956 B2 | 11/2009 | Paul et al. |
| 7,621,958 B2 | 11/2009 | Zdeblick et al. |
| 7,632,282 B2 | 12/2009 | Dinville |
| 7,637,951 B2 | 12/2009 | Michelson |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |

(56) References Cited

U.S. PATENT DOCUMENTS

| | | |
|---|---|---|
| 7,682,396 B2 | 3/2010 | Beaurain et al. |
| 7,695,516 B2 | 4/2010 | Zeegers |
| 7,695,517 B2 | 4/2010 | Benzel et al. |
| 7,695,518 B2 | 4/2010 | Gau |
| 7,708,776 B1 | 5/2010 | Blain et al. |
| 7,717,959 B2 | 5/2010 | William et al. |
| 7,727,280 B2 | 6/2010 | McLuen |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,771,478 B2 | 8/2010 | Navarro et al. |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,896,919 B2 | 3/2011 | Belliard et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,114,082 B2 | 2/2012 | Boyajian et al. |
| 8,147,556 B2 | 4/2012 | Louis et al. |
| 8,162,988 B2 | 4/2012 | Delecrin et al. |
| 8,221,422 B2 | 7/2012 | Mangione |
| 8,221,457 B2 | 7/2012 | Delecrin et al. |
| 8,241,359 B2 | 8/2012 | Davis et al. |
| 8,257,439 B2 | 9/2012 | Zeegers |
| 8,262,700 B2 | 9/2012 | Cho et al. |
| 8,267,999 B2 | 9/2012 | Beaurain et al. |
| 8,343,219 B2 | 1/2013 | Allain et al. |
| 8,388,684 B2 | 3/2013 | Bao et al. |
| 8,409,288 B2 | 4/2013 | Davis et al. |
| 8,430,915 B2 | 4/2013 | Beaurain et al. |
| 8,439,931 B2 | 5/2013 | Dinville |
| 8,465,546 B2 | 6/2013 | Jodaitis et al. |
| 8,623,087 B2 | 1/2014 | Huppert |
| 8,632,591 B2 | 1/2014 | Vila et al. |
| 8,685,100 B2 | 4/2014 | Jodaitis et al. |
| 8,696,709 B2 | 4/2014 | Dinville et al. |
| 8,753,397 B2 | 6/2014 | Beaurain et al. |
| 8,771,284 B2 | 7/2014 | Rashbaum et al. |
| 8,845,691 B2 | 9/2014 | Renaud et al. |
| 8,858,635 B2 | 10/2014 | Hovorka et al. |
| 8,920,474 B2 | 12/2014 | Delecrin et al. |
| 8,974,497 B2 | 3/2015 | Cho et al. |
| 8,974,532 B2 | 3/2015 | Zeegers |
| 8,979,932 B2 | 3/2015 | Rashbaum et al. |
| 9,039,774 B2 | 5/2015 | Chataigner et al. |
| 9,044,339 B2 | 6/2015 | Zeegers |
| 9,078,765 B2 | 7/2015 | Louis et al. |
| 9,144,505 B2 | 9/2015 | Steib |
| 9,173,745 B2 | 11/2015 | Dinville et al. |
| 9,248,025 B2 | 2/2016 | Dinville |
| 9,265,618 B2 | 2/2016 | Rashbaum et al. |
| 9,333,095 B2 | 5/2016 | Beaurain et al. |
| 9,402,658 B2 | 8/2016 | Dinville et al. |
| 9,480,572 B2 | 11/2016 | Jodaitis et al. |
| 9,526,622 B2 | 12/2016 | Vila et al. |
| 9,532,882 B2 | 1/2017 | Huppert |
| 9,597,198 B2 | 3/2017 | Davis et al. |
| 9,655,739 B2 | 5/2017 | Hovorka et al. |
| 9,713,535 B2 | 7/2017 | Davis et al. |
| 9,763,699 B2 | 9/2017 | Beaurain et al. |
| 9,795,485 B2 | 10/2017 | Allain et al. |
| 9,833,331 B2 | 12/2017 | Dinville et al. |
| 9,877,842 B2 | 1/2018 | Chataigner et al. |
| 9,974,661 B2 | 5/2018 | Dinville et al. |
| 2001/0020185 A1 | 9/2001 | Ray |
| 2002/0035400 A1 | 3/2002 | Bryan et al. |
| 2002/0040243 A1 | 4/2002 | Attali et al. |
| 2002/0070565 A1 | 6/2002 | Szapucki et al. |
| 2002/0087212 A1 | 7/2002 | James et al. |
| 2002/0143343 A1 | 10/2002 | Castro |
| 2002/0161375 A1* | 10/2002 | Ralph et al. .................. 606/99 |
| 2002/0161444 A1 | 10/2002 | Choi |
| 2002/0165613 A1 | 11/2002 | Lin et al. |
| 2002/0193880 A1 | 12/2002 | Fraser |
| 2003/0028249 A1 | 2/2003 | Baccelli et al. |
| 2003/0055503 A1 | 3/2003 | O'Neil |
| 2003/0069586 A1* | 4/2003 | Errico et al. .................. 606/99 |
| 2003/0074075 A1 | 4/2003 | Thomas, Jr. et al. |
| 2003/0093153 A1 | 5/2003 | Banick et al. |
| 2003/0093156 A1 | 5/2003 | Metzger et al. |
| 2003/0109928 A1 | 6/2003 | Pasquet et al. |
| 2003/0135279 A1 | 7/2003 | Michelson |
| 2003/0149438 A1 | 8/2003 | Nichols et al. |
| 2003/0171814 A1 | 9/2003 | Muhanna et al. |
| 2003/0187436 A1 | 10/2003 | Bolger et al. |
| 2003/0187506 A1 | 10/2003 | Ross et al. |
| 2003/0195514 A1 | 10/2003 | Trieu et al. |
| 2003/0220691 A1 | 11/2003 | Songer et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1* | 2/2004 | Ralph .................. A61B 17/025 606/90 |
| 2004/0030387 A1 | 2/2004 | Landry et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0083000 A1 | 4/2004 | Keller et al. |
| 2004/0093082 A1 | 5/2004 | Ferree |
| 2004/0093083 A1 | 5/2004 | Branch et al. |
| 2004/0102790 A1 | 5/2004 | Ralph et al. |

(56) References Cited

U.S. PATENT DOCUMENTS

| | | |
|---|---|---|
| 2004/0102846 A1 | 5/2004 | Keller et al. |
| 2004/0111160 A1 | 6/2004 | Evans et al. |
| 2004/0117022 A1 | 6/2004 | Marnay et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0193273 A1 | 9/2004 | Huang |
| 2004/0199254 A1 | 10/2004 | Louis et al. |
| 2004/0210219 A1 | 10/2004 | Bray |
| 2004/0210313 A1 | 10/2004 | Michelson |
| 2004/0225295 A1 | 11/2004 | Zubok et al. |
| 2004/0225363 A1 | 11/2004 | Richelsoph |
| 2004/0225364 A1 | 11/2004 | Richelsoph et al. |
| 2004/0243238 A1 | 12/2004 | Arnin et al. |
| 2004/0243240 A1* | 12/2004 | Beaurain et al. .......... 623/17.14 |
| 2004/0254577 A1 | 12/2004 | Delecrin et al. |
| 2004/0254643 A1 | 12/2004 | Jackson |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz et al. |
| 2005/0038512 A1 | 2/2005 | Michelson |
| 2005/0038516 A1 | 2/2005 | Spoonamore |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marnay et al. |
| 2005/0113926 A1 | 5/2005 | Zucherman et al. |
| 2005/0119665 A1 | 6/2005 | Keller |
| 2005/0131542 A1 | 6/2005 | Benzel et al. |
| 2005/0131544 A1 | 6/2005 | Kuras et al. |
| 2005/0143733 A1 | 6/2005 | Petit |
| 2005/0143824 A1 | 6/2005 | Richelsoph et al. |
| 2005/0143825 A1 | 6/2005 | Enayati |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1* | 7/2005 | Puno .................. A61F 2/4611 606/99 |
| 2005/0165485 A1 | 7/2005 | Trieu |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1* | 9/2005 | Hovorka ............ A61F 2/4425 623/17.15 |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1* | 2/2006 | Peterman .................. 606/99 |
| 2006/0036261 A1 | 2/2006 | Mcdonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Millard |
| 2006/0058878 A1 | 3/2006 | Michelson |
| 2006/0069437 A1 | 3/2006 | Weber |
| 2006/0069441 A1 | 3/2006 | Zucherman et al. |
| 2006/0074432 A1* | 4/2006 | Stad .................. A61F 2/4611 606/90 |
| 2006/0085076 A1 | 4/2006 | Krishna et al. |
| 2006/0085077 A1 | 4/2006 | Cook et al. |
| 2006/0089717 A1 | 4/2006 | Krishna et al. |
| 2006/0095136 A1 | 5/2006 | Mcluen |
| 2006/0111783 A1 | 5/2006 | Aflatoon et al. |
| 2006/0116768 A1* | 6/2006 | Krueger et al. .......... 623/17.14 |
| 2006/0116769 A1 | 6/2006 | Marnay et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0166535 A1* | 7/2006 | Brumfield .......... A61B 17/7088 439/179 |
| 2006/0173544 A1 | 8/2006 | Gau |
| 2006/0178745 A1 | 8/2006 | Bartish et al. |
| 2006/0178746 A1 | 8/2006 | Bartish et al. |
| 2006/0190082 A1 | 8/2006 | Keller et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235520 A1 | 10/2006 | Pannu |
| 2006/0235526 A1 | 10/2006 | Lemaire |
| 2006/0241764 A1 | 10/2006 | Michelson |
| 2006/0253201 A1 | 11/2006 | Mcluen |
| 2006/0259143 A1 | 11/2006 | Navarro et al. |
| 2006/0259147 A1 | 11/2006 | Krishna et al. |
| 2006/0265072 A1 | 11/2006 | Richelsoph |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1* | 4/2007 | Bonutti et al. .................. 606/99 |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1* | 7/2007 | Rashbaum et al. ......... 623/17.11 |
| 2007/0162137 A1 | 7/2007 | Kloss et al. |
| 2007/0168040 A1* | 7/2007 | Raymond .................. 623/17.15 |

(56) References Cited

U.S. PATENT DOCUMENTS

| | | |
|---|---|---|
| 2007/0179623 A1 | 8/2007 | Trieu et al. |
| 2007/0208345 A1* | 9/2007 | Marnay et al. ............... 606/61 |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0293948 A1* | 12/2007 | Bagga et al. ............. 623/17.11 |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1* | 10/2008 | Ralph et al. .................. 606/99 |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2008/0312743 A1 | 12/2008 | Villa et al. |
| 2009/0005874 A1* | 1/2009 | Fleischmann et al. .... 623/17.16 |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0010547 A1 | 1/2010 | Beaurain et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0053693 A1 | 3/2012 | Zeegers |
| 2012/0116466 A1 | 5/2012 | Dinville et al. |
| 2012/0330424 A1 | 12/2012 | Zeegers |
| 2013/0013006 A1 | 1/2013 | Rashbaum et al. |
| 2013/0150968 A1 | 6/2013 | Dinville et al. |
| 2013/0166029 A1 | 6/2013 | Dinville et al. |
| 2013/0226300 A1 | 8/2013 | Chataigner et al. |
| 2013/0253648 A1 | 9/2013 | Beaurain et al. |
| 2013/0253651 A1 | 9/2013 | Dinville |
| 2013/0282124 A1 | 10/2013 | Jodaitis et al. |
| 2014/0114413 A1 | 4/2014 | Allain et al. |
| 2014/0135935 A1 | 5/2014 | Vila et al. |
| 2015/0051702 A1 | 2/2015 | Chataigner et al. |
| 2015/0080959 A1 | 3/2015 | Renaud et al. |
| 2017/0112636 A1 | 4/2017 | Jodaitis et al. |

FOREIGN PATENT DOCUMENTS

| | | | |
|---|---|---|---|
| CA | 2677598 | A1 | 8/2008 |
| CA | 2533473 | C | 3/2011 |
| CA | 2677598 | C | 1/2015 |
| DE | 2263842 | A1 | 7/1974 |
| DE | 2804936 | A1 | 8/1979 |
| DE | 3023353 | A1 | 4/1981 |
| DE | 8912648 | U1 | 11/1990 |
| DE | 4328690 | A1 | 3/1995 |
| DE | 29911422 | U1 | 8/1999 |
| DE | 20310432 | U1 | 9/2003 |
| DE | 20310433 | U1 | 9/2003 |
| DE | 20320454 | U1 | 10/2004 |

(56) References Cited

FOREIGN PATENT DOCUMENTS

| | | |
|---|---|---|
| DE | 10323363 A1 | 12/2004 |
| DE | 102004027986 A1 | 7/2005 |
| EP | 42271 A1 | 12/1981 |
| EP | 176728 A1 | 4/1986 |
| EP | 0298235 A1 | 1/1989 |
| EP | 0317972 A1 | 5/1989 |
| EP | 0333990 A2 | 9/1989 |
| EP | 0356112 A1 | 2/1990 |
| EP | 0512529 A1 | 11/1992 |
| EP | 0560141 A1 | 9/1993 |
| EP | 0566810 A1 | 10/1993 |
| EP | 0637439 A1 | 2/1995 |
| EP | 0697200 A1 | 2/1996 |
| EP | 0566810 B1 | 8/1996 |
| EP | 0738504 A1 | 10/1996 |
| EP | 0747025 A1 | 12/1996 |
| EP | 0852934 A1 | 7/1998 |
| EP | 0903126 A1 | 3/1999 |
| EP | 0951879 A2 | 10/1999 |
| EP | 0955021 A1 | 11/1999 |
| EP | 0978258 A1 | 2/2000 |
| EP | 1222903 A1 | 7/2002 |
| EP | 1250898 A1 | 10/2002 |
| EP | 1287795 A1 | 3/2003 |
| EP | 1344506 A1 | 9/2003 |
| EP | 1344508 A1 | 9/2003 |
| EP | 1504733 A1 | 2/2005 |
| EP | 1374808 B1 | 12/2005 |
| EP | 1504733 B1 | 6/2007 |
| EP | 2117472 A2 | 11/2009 |
| FR | 2124815 A5 | 9/1972 |
| FR | 2372622 A1 | 6/1978 |
| FR | 2659226 A2 | 9/1991 |
| FR | 2716619 A1 | 9/1995 |
| FR | 2718635 A1 | 10/1995 |
| FR | 2723841 A1 | 3/1996 |
| FR | 2724108 A1 | 3/1996 |
| FR | 2730159 A1 | 8/1996 |
| FR | 2737656 A1 | 2/1997 |
| FR | 2632516 A1 | 12/1999 |
| FR | 2787019 A1 | 6/2000 |
| FR | 2787021 A1 | 6/2000 |
| FR | 2824261 A1 | 11/2002 |
| FR | 2831796 A1 | 5/2003 |
| FR | 2843293 A1 | 2/2004 |
| FR | 2846550 A1 | 5/2004 |
| FR | 2865629 A1 | 8/2005 |
| FR | 2865630 A1 | 8/2005 |
| FR | 2869528 A1 | 11/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2916956 A1 | 12/2008 |
| JP | 2261446 A | 10/1990 |
| WO | WO-9011740 A1 | 10/1990 |
| WO | WO-1991007931 A1 | 6/1991 |
| WO | WO-9113598 A1 | 9/1991 |
| WO | WO-9301771 A1 | 2/1993 |
| WO | WO-9404100 A1 | 3/1994 |
| WO | WO-9515133 A1 | 6/1995 |
| WO | WO-9817209 A2 | 4/1998 |
| WO | WO-9909914 A1 | 3/1999 |
| WO | WO-1999053871 A1 | 10/1999 |
| WO | WO-9956675 A1 | 11/1999 |
| WO | WO-9956676 A1 | 11/1999 |
| WO | WO-1999065412 A1 | 12/1999 |
| WO | WO-1999066864 A1 | 12/1999 |
| WO | WO-0053127 A1 | 9/2000 |
| WO | WO-0074606 A1 | 12/2000 |
| WO | WO-0101893 A1 | 1/2001 |
| WO | WO-0119295 A1 | 3/2001 |
| WO | WO-0143620 A2 | 6/2001 |
| WO | WO-2001041680 A1 | 6/2001 |
| WO | WO-2001062191 A2 | 8/2001 |
| WO | WO-0213732 A2 | 2/2002 |
| WO | WO-02058599 A2 | 8/2002 |
| WO | WO-2002071960 A1 | 9/2002 |
| WO | WO-02089701 A2 | 11/2002 |
| WO | WO-2002089701 A2 | 11/2002 |
| WO | WO-03005939 A2 | 1/2003 |
| WO | WO-2003015646 A1 | 2/2003 |
| WO | WO-03026522 A2 | 4/2003 |
| WO | WO-2003026522 A2 | 4/2003 |
| WO | WO-03039400 A2 | 5/2003 |
| WO | WO-2003045262 A2 | 6/2003 |
| WO | WO-03059212 A1 | 7/2003 |
| WO | WO-03075804 A1 | 9/2003 |
| WO | WO-2003075803 A1 | 9/2003 |
| WO | WO-03099172 A1 | 12/2003 |
| WO | WO-2004034935 A1 | 4/2004 |
| WO | WO-2004039291 A1 | 5/2004 |
| WO | WO-2004041129 A1 | 5/2004 |
| WO | WO-2004041131 A2 | 5/2004 |
| WO | WO-2004071360 A2 | 8/2004 |
| WO | WO-2004089256 A1 | 10/2004 |
| WO | WO-2005007040 A1 | 1/2005 |
| WO | WO-2005007044 A1 | 1/2005 |
| WO | WO-2005046534 A1 | 5/2005 |
| WO | WO-2005051243 A2 | 6/2005 |
| WO | WO-2005063150 A1 | 7/2005 |
| WO | WO-2005074839 A1 | 8/2005 |
| WO | WO-05104996 A1 | 11/2005 |
| WO | WO-2005117728 A1 | 12/2005 |
| WO | WO-2006016384 A1 | 2/2006 |
| WO | WO-2006047587 A2 | 5/2006 |
| WO | WO-2006062960 A2 | 6/2006 |
| WO | WO-2006120505 A1 | 11/2006 |
| WO | WO-2006130460 A2 | 12/2006 |
| WO | WO-2006136760 | 12/2006 |
| WO | WO-2007000654 A2 | 1/2007 |
| WO | WO-2006130460 A3 | 3/2007 |
| WO | WO-2007034310 A1 | 3/2007 |
| WO | WO-2007063398 A2 | 6/2007 |
| WO | WO-2007078978 A2 | 7/2007 |
| WO | WO-2008099277 A3 | 8/2008 |
| WO | WO-2008149223 A2 | 12/2008 |
| WO | WO-2009033100 A1 | 3/2009 |
| WO | WO-2011080535 A1 | 7/2011 |
| WO | WO-2013124453 A1 | 8/2013 |

OTHER PUBLICATIONS

"U.S. Appl. No. 10/476,565, Amendment After Final filed Nov. 29, 2007", 1 pg.

"U.S. Appl. No. 10/476,565, Final Office Action dated May 7, 2007", 8 pgs.

"U.S. Appl. No. 10/476,565, Non Final Office Action dated Jul. 18, 2006", 9 pgs.

"U.S. Appl. No. 10/476,565, Notice of Allowance dated Nov. 29, 2007", 4 pgs.

"U.S. Appl. No. 10/476,565, Response filed Jan. 17, 2007 to Non Final Office Action Jul. 18, 2006", 23 pgs.

"U.S. Appl. No. 10/476,565, Response filed Nov. 6, 2007 to Final Office Action May 7, 2007", 37 pgs.

"U.S. Appl. No. 10/494,418, Notice of Allowance dated Sep. 20, 2005", 12 pgs.

"U.S. Appl. No. 10/533,846, Final Office Action dated Oct. 15, 2008", 13 pgs.

"U.S. Appl. No. 10/533,846, Non Final Office Action dated Apr. 18, 2007", 11 pgs.

"U.S. Appl. No. 10/533,846, Non Final Office Action dated Dec. 26, 2007", 14 pgs.

"U.S. Appl. No. 10/533,846, Notice of Allowance dated Nov. 4, 2009", 4 pgs.

"U.S. Appl. No. 10/533,846, Response filed Apr. 15, 2009 to Final Office Action dated Oct. 15, 2008", 13 pgs.

"U.S. Appl. No. 10/533,846, Response filed Jun. 25, 2008 to Non Final Office Action dated Dec. 26, 2007", 18 pgs.

(56) References Cited

OTHER PUBLICATIONS

"U.S. Appl. No. 10/533,846, Response filed Oct. 16, 2007 to Non Final Office Action dated Apr. 18, 2007", 16 pgs.
"U.S. Appl. No. 11/051,710, Appeal Brief filed Jan. 15, 2013", 27 pgs.
"U.S. Appl. No. 11/051,710, Final Office Action dated Jul. 20, 2010", 9 pgs.
"U.S. Appl. No. 11/051,710, Final Office Action dated Dec. 15, 2011", 9 pgs.
"U.S. Appl. No. 11/051,710, Non Final Office Action dated Apr. 11, 2011", 9 pgs.
"U.S. Appl. No. 11/051,710, Non Final Office Action dated Oct. 26, 2009", 12 pgs.
"U.S. Appl. No. 11/051,710, Notice of Allowance dated Apr. 11, 2013", 9 pgs.
"U.S. Appl. No. 11/051,710, Notice of Allowance dated Jun. 11, 2014", 6 pgs.
"U.S. Appl. No. 11/051,710, Response filed Jan. 20, 2011 to Final Office Action dated Jul. 20, 2010", 19 pgs.
"U.S. Appl. No. 11/051,710, Response filed Apr. 26, 2010 to Non Final Office Action dated Oct. 26, 2011", 19 pgs.
"U.S. Appl. No. 11/051,710, Response filed Oct. 11, 2011 to Non Final Office Action dated Apr. 11, 2011", 19 pgs.
"U.S. Appl. No. 11/098,266, Final Office Action dated Aug. 6, 2007", 8 pgs.
"U.S. Appl. No. 11/098,266, Non Final Office Action dated Mar. 22, 2006", 5 pgs.
"U.S. Appl. No. 11/098,266, Non Final Office Action dated Nov. 29, 2006", 5 pgs.
"U.S. Appl. No. 11/098,266, Notice of Allowance dated Apr. 21, 2008", 7 pgs.
"U.S. Appl. No. 11/098,266, Response filed Feb. 6, 2008 to Final Office Action dated Aug. 6, 2007", 14 pgs.
"U.S. Appl. No. 11/098,266, Response filed May 23, 2007 to Non Final Office Action dated Nov. 29, 2006", 10 pgs.
"U.S. Appl. No. 11/098,266, Response filed Aug. 22, 2006 to Non Final Office Action dated Mar. 22, 2006", 17 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Notice of Allowance dated Dec. 8, 2009", 8 pgs.
"U.S. Appl. No. 11/109,276, Response filed Jan. 26, 2009 to Final Office Action dated Jul. 24, 2008", 9 pgs.
"U.S. Appl. No. 11/109,276, Response filed Apr. 16, 2008 to Non Final Office Action dated Oct. 16, 2017", 16 pgs.
"U.S. Appl. No. 11/109,276, Response filed Aug. 4, 2009 to Non Final Office Action dated Feb. 13, 2009", 8 pgs.
"U.S. Appl. No. 11/109,276, Response filed Aug. 6, 2007 to Non Final Office Action dated Feb. 6, 2007", 39 pgs.
"U.S. Appl. No. 11/180,868, Final Office Action dated Nov. 5, 2008", 10 pgs.
"U.S. Appl. No. 11/180,868, Non Final Office Action dated Jan. 22, 2008", 15 pgs.
"U.S. Appl. No. 11/180,868, Notice of Allowance dated Jul. 17, 2009", 5 pgs.
"U.S. Appl. No. 11/180,868, Notice of Allowance dated Jul. 31, 2009", 6 pgs.
"U.S. Appl. No. 11/180,868, Response filed May 5, 2009 to Final Office Action dated Nov. 5, 2008", 11 pgs.
"U.S. Appl. No. 11/180,868, Response filed Jul. 21, 2008 to Non Final Office Action dated Jan. 22, 2008", 15 pgs.
"U.S. Appl. No. 11/341,007, Final Office Action dated Dec. 17, 2009", 17 pgs.
"U.S. Appl. No. 11/341,007, Non Final Office Action dated Apr. 13, 2009", 13 pgs.
"U.S. Appl. No. 11/341,007, Notice of Allowance dated Jul. 26, 2010", 6 pgs.
"U.S. Appl. No. 11/341,007, Response filed Jun. 17, 2010 to Final Office Action dated Dec. 17, 2009", 12 pgs.
"U.S. Appl. No. 11/341,007, Response filed Oct. 13, 2009 to Non Final Office Action dated Apr. 13, 2009", 15 pgs.
"U.S. Appl. No. 11/362,253, Appeal Brief filed Apr. 9, 2012", 38 pgs.
"U.S. Appl. No. 11/362,253, Examiners Answer dated Jun. 20, 2012", 18 pgs.
"U.S. Appl. No. 11/362,253, Final Office Action dated Mar. 8, 2011", 18 pgs.
"U.S. Appl. No. 11/362,253, Final Office Action dated Oct. 15, 2009", 15 pgs.
"U.S. Appl. No. 11/362,253, Non Final Office Action dated Feb. 18, 2009", 14 pgs.
"U.S. Appl. No. 11/362,253, Non Final Office Action dated Jun. 18, 2010", 17 pgs.
"U.S. Appl. No. 11/362,253, Reply Brief filed Aug. 20, 2012", 18 pgs.
"U.S. Appl. No. 11/362,253, Response filed Apr. 15, 2010 to Final Office Action dated Oct. 15, 2009", 24 pgs.
"U.S. Appl. No. 11/362,253, Response filed Aug. 18, 2009 to Non Final Office Action dated Feb. 18, 2009", 15 pgs.
"U.S. Appl. No. 11/362,253, Response filed Aug. 18, 2009 to Office Action dated Feb. 18, 2009", 15 pgs.
"U.S. Appl. No. 11/362,253, Response filed Dec. 20, 2010 to Non Final Office Action dated Jun. 18, 2010", 18 pgs.
"U.S. Appl. No. 11/676,237, Appeal Brief filed Oct. 17, 2011", 41 pgs.
"U.S. Appl. No. 11/676,237, Final Office Action dated Sep. 15, 2010", 12 pgs.
"U.S. Appl. No. 11/676,237, Final Office Action dated Nov. 6, 2012", 6 pgs.
"U.S. Appl. No. 11/676,237, Non Final Office Action dated Feb. 16, 2012", 13 pgs.
"U.S. Appl. No. 11/676,237, Non Final Office Action dated Mar. 20, 2009", 10 pgs.
"U.S. Appl. No. 11/676,237, Non Final Office Action dated Dec. 18, 2009", 11 pgs.
"U.S. Appl. No. 11/676,237, Notice of Allowance dated Feb. 20, 2013", 5 pgs.
"U.S. Appl. No. 11/676,237, Response filed Feb. 6, 2013 to Final Office Action dated Nov. 6, 2012", 9 pgs.
"U.S. Appl. No. 11/676,237, Response filed Jun. 18, 2010 to Non Final Office Action dated Dec. 18, 2009", 15 pgs.
"U.S. Appl. No. 11/676,237, Response filed Jul. 16, 2012 to Non Final Office Action dated Feb. 16, 2012", 11 pgs.
"U.S. Appl. No. 11/676,237, Response filed Sep. 21, 2009 to Non Final Office Action dated Mar. 20, 2009", 13 pgs.
"U.S. Appl. No. 12/025,677, Final Office Action dated Jun. 29, 2012", 8 pgs.
"U.S. Appl. No. 12/025,677, Final Office Action dated Nov. 7, 2014", 12 pgs.
"U.S. Appl. No. 12/025,677, Non Final Office Action dated Feb 19, 2014", 11 pgs.
"U.S. Appl. No. 12/025,677, Non Final Office Action dated Jun. 20, 2013", 8 pgs.
"U.S. Appl. No. 12/025,677, Non Final Office Action dated Oct. 7, 2014", 9 pgs.
"U.S. Appl. No. 12/025,677, Response filed Apr. 9, 2012 to Non Final Office Action dated Oct. 7, 2011", 16 pgs.
"U.S. Appl. No. 12/025,677, Response filed Aug. 19, 2014 to Non Final Office Action dated Feb. 19, 2014", 23 pgs.
"U.S. Appl. No. 12/025,677, Response filed Dec. 20, 2013 to Non Final Office Action dated Jun. 20, 2013", 21 pgs.
"U.S. Appl. No. 12/025,677, Response filed Dec. 29, 2012 to Final Office Action dated Jun. 29, 2012", 20 pgs.
"U.S. Appl. No. 12/134,884, Non Final Office Action dated Jan. 31, 2012", 7 pgs.

(56) References Cited

OTHER PUBLICATIONS

"U.S. Appl. No. 12/134,884, Notice of Allowance dated Nov. 1, 2012", 7 pgs.
"U.S. Appl. No. 12/134,884, Response filed Jul. 31, 2012 to Non Final Office Action dated Jan. 31, 2012", 20 pgs.
"U.S. Appl. No. 12/360,050, Non Final Office Action dated Sep. 6, 2011", 11 pgs.
"U.S. Appl. No. 12/360,050, Non Final Office Action dated Dec. 17, 2010", 14 pgs.
"U.S. Appl. No. 12/360,050, Notice of Allowance dated Mar. 26, 2012", 5 pgs.
"U.S. Appl. No. 12/360,050, Notice of Allowance dated May 18, 2012", 4 pgs.
"U.S. Appl. No. 12/360,050, Notice of Allowance dated Jul. 6, 2012", 5 pgs.
"U.S. Appl. No. 12/360,050, Notice of Allowance dated Aug. 2, 2012", 2 pgs.
"U.S. Appl. No. 12/360,050, Response filed Mar. 6, 2012 to Non Final Office Action dated Sep. 6, 2011", 14 pgs.
"U.S. Appl. No. 12/360,050, Response filed Jun. 16, 2011 to Non Final Office Action dated Dec. 17, 2010", 34 pgs.
"U.S. Appl. No. 12/391,086, Non Final Office Action dated Jul. 29, 2010", 10 pgs.
"U.S. Appl. No. 12/391,086, Notice of Allowance dated Apr. 15, 2011", 6 pgs.
"U.S. Appl. No. 12/391,086, Response filed Jan. 31, 2011 to Non Final Office Action dated Jul. 29, 2010", 16 pgs.
"U.S. Appl. No. 12/424,364, Applicant's Summary of Examiner Interview filed May 22, 2012", 3 pgs.
"U.S. Appl. No. 12/424,364, Non Final Office Action dated Jan. 26, 2012", 10 pgs.
"U.S. Appl. No. 12/424,364, Non Final Office Action dated May 18, 2011", 10 pgs.
"U.S. Appl. No. 12/424,364, Non Final Office Action dated May 23, 2012", 6 pgs.
"U.S. Appl. No. 12/424,364, Notice of Allowance dated Jul. 24, 2012", 5 pgs.
"U.S. Appl. No. 12/424,364, Notice of Allowance dated Aug. 2, 2012", 2 pgs.
"U.S. Appl. No. 12/424,364, Response filed Feb. 27, 2012 to Non Final Office Action dated Jan. 26, 2012", 6 pgs.
"U.S. Appl. No. 12/424,364, Response filed Jul. 6, 2012 to Non Final Office Action dated May 23, 2012", 4 pgs.
"U.S. Appl. No. 12/424,364, Response filed Nov. 18, 2011 to Non Final Office Action dated May 18, 2011", 13 pgs.
"U.S. Appl. No. 12/435,955, Final Office Action dated Jul. 23, 2012", 9 pgs.
"U.S. Appl. No. 12/435,955, Non Final Office Action dated Oct. 11, 2011", 8 pgs.
"U.S. Appl. No. 12/435,955, Notice of Allowance dated Jan. 16, 2013", 5 pgs.
"U.S. Appl. No. 12/435,955, Response filed Apr. 11, 2012 to Non Final Office Action dated Oct. 11, 2011", 12 pgs.
"U.S. Appl. No. 12/435,955, Response filed Dec. 24, 2012 to Final Office Action dated Jul. 23, 2012", 13 pgs.
"U.S. Appl. No. 12/527,373, 312 Amendment filed Dec. 2, 2013", Request for Continued Examination, 4 pgs.
"U.S. Appl. No. 12/527,373, Appeal Brief filed Apr. 24, 2013", 15 pgs.
"U.S. Appl. No. 12/527,373, Applicant's Summary of Examiner Interview filed Jan. 31, 2014", 3 pgs.
"U.S. Appl. No. 12/527,373, Final Office Action dated Sep. 24, 2012", 8 pgs.
"U.S. Appl. No. 12/527,373, Non Final Office Action dated Dec. 21, 2011", 7 pgs.
"U.S. Appl. No. 12/527,373, Notice of Allowance dated Aug. 30, 2013", 13 pgs.
"U.S. Appl. No. 12/527,373, Notice of Allowance dated Dec. 24, 2013", 8 pgs.
"U.S. Appl. No. 12/527,373, Preliminary Amendment filed Aug. 14, 2009", 5 pgs.
"U.S. Appl. No. 12/527,373, Response filed Jun. 21, 2012 to Non Final Office Action dated Dec. 21, 2011", 15 pgs.
"U.S. Appl. No. 12/955,898, Final Office Action dated Jan. 10, 2013", 17 pgs.
"U.S. Appl. No. 12/955,898, Non Final Office Action dated Mar. 3, 2014", 11 pgs.
"U.S. Appl. No. 12/955,898, Non Final Office Action dated Jun. 1, 2012", 27 pgs.
"U.S. Appl. No. 12/955,898, Notice of Allowance dated Aug. 8, 2014", 7 pgs.
"U.S. Appl. No. 12/955,898, Response filed Apr. 19, 2012 to Restriction Requirement dated Mar. 19, 2012", 11 pgs.
"U.S. Appl. No. 12/955,898, Response filed Jul. 10, 2013 to Final Office Action dated Jan. 10, 2013", 12 pgs.
"U.S. Appl. No. 12/955,898, Response filed Aug. 4, 2014 to Non Final Office Action dated Mar. 3, 2014", 11 pgs.
"U.S. Appl. No. 12/955,898, Response filed Dec. 3, 2012 to Non Final Office Action dated Jun. 1, 2012", 20 pgs.
"U.S. Appl. No. 12/955,898, Restriction Requirement dated Mar. 19, 2012", 9 pgs.
"U.S. Appl. No. 13/158,761, Examiner Interview Summary dated Aug. 1, 2013", 3 pgs.
"U.S. Appl. No. 13/158,761, Examiner Interview Summary dated Oct. 31, 2012", 3 pgs.
"U.S. Appl. No. 13/158,761, Final Office Action dated Aug. 14, 2013", 11 pgs.
"U.S. Appl. No. 13/158,761, Non Final Office Action dated Feb. 28, 2013", 10 pgs.
"U.S. Appl. No. 13/158,761, Response filed Jul. 29, 2013 to Non Final Office Action dated Feb. 28, 2013", 12 pgs.
"U.S. Appl. No. 13/158,761, Response filed Nov. 14, 2013 to Final Office Action dated Aug. 14, 2013", 12 pgs.
"U.S. Appl. No. 13/158,761, Response filed Nov. 19, 2012 to Restriction Requirement dated Oct. 17, 2012", 8 pgs.
"U.S. Appl. No. 13/158,761, Restriction Requirement dated Oct. 17, 2012", 6 pgs.
"U.S. Appl. No. 13/215,123, Final Office Action dated Nov. 18, 2013", 8 pgs.
"U.S. Appl. No. 13/215,123, Non Final Office Action dated May 24, 2013", 17 pgs.
"U.S. Appl. No. 13/215,123, Non Final Office Action dated Nov. 20, 2012", 7 pgs.
"U.S. Appl. No. 13/215,123, Notice of Allowance dated Aug. 29, 2014", 7 pgs.
"U.S. Appl. No. 13/215,123, Response filed Mar. 20, 2013 to Non Final Office Action dated Nov. 20, 2012", 9 pgs.
"U.S. Appl. No. 13/215,123, Response filed May 19, 2014 to Final Office Action dated Nov. 18, 2013", 9 pgs.
"U.S. Appl. No. 13/215,123, Response filed Oct. 24, 2013 to Non Final Office Action dated May 24, 2013", 15 pgs.
"U.S. Appl. No. 13/215,123, Supplemental Amendment filed Nov. 11, 2013", 3 pgs.
"U.S. Appl. No. 13/603,043, Final Office Action dated Jul. 24, 2014", 11 pgs.
"U.S. Appl. No. 13/603,043, Non Final Office Action dated Apr. 9, 2013", 13 pgs.
"U.S. Appl. No. 13/603,043, Non Final Office Action dated Nov. 21, 2013", 11 pgs.
"U.S. Appl. No. 13/603,043, Response filed May 21, 2014 to Non Final Office Action dated Nov. 21, 2013", 13 pgs.
"U.S. Appl. No. 13/603,043, Response filed Oct. 9, 2013 to Non Final Office Action dated Apr. 9, 2013", 37 pgs.
"U.S. Appl. No. 13/616,448, Non Final Office Action dated Aug. 22, 2013", 6 pgs.
"U.S. Appl. No. 13/616,448, Notice of Allowance dated Feb. 7, 2014", 5 pgs.
"U.S. Appl. No. 13/620,797, Non Final Office Action dated Jul. 5, 2013", 6 pgs.
"U.S. Appl. No. 13/620,797, Notice of Allowance dated Jan. 29, 2014", 5 pgs.

(56) References Cited

OTHER PUBLICATIONS

"U.S. Appl. No. 13/620,797, Response filed Nov. 5, 2013 to Non Final Office Action dated Jul. 5, 2013", 9 pgs.
"U.S. Appl. No. 13/892,933, Final Office Action dated Jul. 28, 2014", 7 pgs.
"U.S. Appl. No. 13/892,933, Non Final Office Action dated Jan. 2, 2014", 6 pgs.
"U.S. Appl. No. 13/892,933, Response filed Apr. 2, 2014 to Non Final Office Action dated Jan. 2, 2014", 10 pgs.
"U.S. Appl. No. 13/919,704, 312 Amendment filed Jul. 29, 2016", 11 pgs.
"U.S. Appl. No. 13/919,704, Corrected Notice of Allowance dated Sep. 7, 2016", 2 pgs.
"U.S. Appl. No. 13/919,704, Final Office Action dated Jun. 2, 2014", 12 pgs.
"U.S. Appl. No. 13/919,704, Final Office Action dated Dec. 29, 2015", 11 pgs.
"U.S. Appl. No. 13/919,704, Non Final Office Action dated Mar. 13, 2015", 11 pgs.
"U.S. Appl. No. 13/919,704, Non Final Office Action dated Oct. 31, 2013", 10 pgs.
"U.S. Appl. No. 13/919,704, Notice of Allowance dated Jun. 15, 2016", 8 pgs.
"U.S. Appl. No. 13/919,704, Preliminary Amendment filed Jun. 17, 2013", 8 pgs.
"U.S. Appl. No. 13/919,704, Response filed Jan. 31, 2014 to Non Final Office Action dated Oct. 31, 2013", 15 pgs.
"U.S. Appl. No. 13/919,704, Response filed Apr. 29, 2016 to Final Office Action dated Dec. 29, 2015", 10 pgs.
"U.S. Appl. No. 13/919,704, Response filed Sep. 14, 2015 to Non Final Office Action dated Mar. 13, 2015", 11 pgs.
"U.S. Appl. No. 13/919,704, Response filed Dec. 2, 2014 to Final Office Action dated Jun. 2, 2014", 13 pgs.
"U.S. Appl. No. 14/306,785, Non Final Office Action dated Oct. 22, 2014", 6 pgs.
"U.S. Appl. No. 15/340,565, Final Office Action dated May 10, 2018", 12 pgs.
"U.S. Appl. No. 15/340,565, Non Final Office Action dated Sep. 12, 2017", 12 pgs.
"U.S. Appl. No. 15/340,565, Preliminary Amendment filed Nov. 1, 2016", 7 pgs.
"U.S. Appl. No. 15/340,565, Response filed Jun. 29, 2018 to Final Office Action dated May 10, 2018", 8 pgs.
"U.S. Appl. No. 15/340,565, Response filed Dec. 12, 2017 to Non Final Office Action dated Sep. 12, 2017", 14 pgs.
"Australian Application Serial No. 2008215916, First Examination Report dated Nov. 16, 2010", 2 pgs.
"Australian Application Serial No. 2008215916, Response filed Oct. 31, 2011 to First Examination Report dated Nov. 16, 2010", 9 pgs.
"Canadian Application Serial No. 2,677,598, Office Action dated Aug. 26, 2013", 2 pgs.
"Canadian Application Serial No. 2,677,598, Response filed Feb. 26, 2014 to Office Action dated Aug. 26, 2013", 6 pgs.
"Canadian Application Serial No. 2,677,598, Voluntary Amendment filed Aug. 6, 2009", 4 pgs.
"European Application Serial No. 05702425.9, Communication Pursuant to Article 94(3) EPC dated Mar. 2, 2009", 3 pgs.
"European Application Serial No. 05702425.9, Notice of Intention to Grant dated Oct. 22, 2010", 35 pgs.
"European Application Serial No. 05702425.9, Response filed 07-22-09 to Communication Pursuant to Article 94(3) EPC dated Mar. 2, 2009", 16 pgs.
"European Application Serial No. 05857774.3, Communication Pursuant to Article 94(3) EPC dated Apr. 11, 2011", 4 pgs.
"European Application Serial No. 05857774.3, Communication Pursuant to Article 94(3) EPC dated May 6, 2009", 3 pgs.
"European Application Serial No. 05857774.3, Response filed Oct. 11, 2011 to Communication Pursuant to Article 94(3) EPC dated Apr. 11, 2011", 20 pgs.
"European Application Serial No. 05857774.3, Response filed Nov. 13, 2009 to Communication Pursuant to Article 94(3) EPC dated May 6, 2009", 22 pgs.
"European Application Serial No. 08709823.2, Communication pursuant to Article 94(3) EPC dated Jul. 19, 2013", 4 pgs.
"European Application Serial No. 08709823.2, Response filed Jan. 28, 2014 to Communication pursuant to Article 94(3) EPC dated Jul. 19, 2013", 21 pgs.
"European Application Serial No. 10185004.8, Extended European Search Report dated Apr. 6, 2011", 6 pgs.
"European Application Serial No. 11165170.9, Communication Pursuant to Article 94(3) EPC May 15, 2012", 5 pgs.
"European Application Serial No. 11165170.9, Extended European Search Report dated Jul. 21, 2011", 7 pgs.
"European Application Serial No. 11165170.9, Response filed Mar. 6, 2012 to Extended European Search Report mailed Jul. 21, 2011", 17 pgs.
"European Application Serial No. 13170071.8, Extended European Search Report dated Oct. 1, 2013", 6 pgs.
"France Application Serial No. 0213833, Preliminary Search Report dated Jul. 10, 2003", 2 pgs.
"France Application Serial No. 0413728, Preliminary Search Report dated Aug. 11, 2005", 2 pgs.
"France Application Serial No. 0509740, Preliminary Search Report dated Jun. 27, 2006", 2 pgs.
"France Application Serial No. 0512133, Preliminary Search Report dated Aug. 4, 2006", 2 pgs.
"France Application Serial No. 0704155, Preliminary Search Report dated Jan. 30, 2008", 3 pgs.
"France Application Serial No. 2730159, Preliminary Search Report dated Sep. 29, 1995", 1 pg.
"France Application Serial No. 2824261, Preliminary Search Report dated Feb. 25, 2002", 4 pgs.
"France Application Serial No. 2831796, Preliminary Search Report dated Aug. 2, 2002", 2 pgs.
"France Application Serial No. 2865629, Preliminary Search Report dated Sep. 14, 2004", 2 pgs.
"France Application Serial No. 2865630, Preliminary Search Report dated Jan. 12, 2005", 2 pgs.
"France Application Serial No. 2869528, Preliminary Search Report dated Dec. 13, 2004", 3 pgs.
"France Application Serial No. 9404832, Preliminary Search Report dated Jan. 16, 1995", 1 pg.
"International Application Serial No. PCT/IB2002/002998, International Preliminary Examination Report dated Dec. 22, 2003", 8 pgs.
"International Application Serial No. PCT/IB2002/002998, International Search Report dated Sep. 16, 2003", 6 pgs.
"International Application Serial No. PCT/IB2002/004642, International Preliminary Examination Report dated Apr. 1, 2004", 4 pgs.
"International Application Serial No. PCT/IB2002/004642, International Search Report dated Jul. 2, 2003", 2 pgs.
"International Application Serial No. PCT/IB2003/004872, International Preliminary Examination Report dated Mar. 1, 2005", 6 pgs.
"International Application Serial No. PCT/IB2003/004872, International Search Report dated Mar. 3, 2004", 3 pgs.
"International Application Serial No. PCT/IB2005/000280, International Preliminary Report on Patentability dated Jan. 16, 2006", 8 pgs.
"International Application Serial No. PCT/IB2005/000280, International Search Report dated Jun. 24, 2005", 5 pgs.
"International Application Serial No. PCT/IB2005/000280, Written Opinion dated Jun. 24, 2005", 8 pgs.
"International Application Serial No. PCT/IB2005/001151, International Preliminary Report on Patentability dated Jun. 28, 2006", 5 pgs.
"International Application Serial No. PCT/IB2005/001151, International Search Report dated Sep. 12, 2005", 3 pgs.
"International Application Serial No. PCT/IB2005/001151, Written Opinion dated Sep. 12, 2005", 5 pgs.

(56) References Cited

OTHER PUBLICATIONS

"International Application Serial No. PCT/IB2005/004093, International Preliminary Report on Patentability dated Feb. 22, 2007", 8 pgs.
"International Application Serial No. PCT/IB2005/004093, International Search Report dated Aug. 31, 2006", 3 pgs.
"International Application Serial No. PCT/IB2005/004093, Written Opinion dated Aug. 31, 2006", 5 pgs.
"International Application Serial No. PCT/IB2006/001781, International Preliminary Report on Patentability dated Jul. 19, 2007", 6 pgs.
"International Application Serial No. PCT/IB2006/001781, International Search Report dated Mar. 22, 2007", 3 pgs.
"International Application Serial No. PCT/IB2006/001781, Written Opinion dated Mar. 22, 2007", 6 pgs.
"International Application Serial No. PCT/IB2006/002632, International Preliminary Report on Patentability dated Aug. 14, 2007", 5 pgs.
"International Application Serial No. PCT/IB2006/002632, International Search Report dated Feb. 23, 2007", 3 pgs.
"International Application Serial No. PCT/IB2006/002632, Written Opinion dated Feb. 23, 2007", 5 pgs.
"International Application Serial No. PCT/IB2006/003418, International Preliminary Report on Patentability dated Nov. 12, 2007", 8 pgs.
"International Application Serial No. PCT/IB2006/003418, International Search Report dated Jul. 24, 2007", 6 pgs.
"International Application Serial No. PCT/IB2006/003418, Written Opinion dated Jul. 24, 2007", 8 pgs.
"International Application Serial No. PCT/IB2008/000349, International Preliminary Report on Patentability dated May 29, 2009", 10 pgs.
"International Application Serial No. PCT/IB2008/000349, International Search Report dated Jan. 12, 2007", 7 pgs.
"International Application Serial No. PCT/IB2008/000349, Written Opinion dated Jan. 12, 2009", 10 pgs.
"International Application Serial No. PCT/IB2008/000349, Written Opinion dated Aug. 16, 2009", 10 pgs.
"International Application Serial No. PCT/IB2008/001484, International Preliminary Report on Patentability dated Aug. 5, 2009", 6 pgs.
"International Application Serial No. PCT/IB2008/001484, International Search Report dated Feb. 16, 2009", 5 pgs.
"International Application Serial No. PCT/IB2008/001484, Written Opinion dated Feb. 16, 2009", 8 pgs.
"International Application Serial No. PCT/IB2009/008048, International Search Report dated Feb. 2, 2011", 6 pgs.
"LDR Medical, by its attorneys; Chapter II amendments for PCT Pub'n No. WO2006120505", App. No. PCT/IB2005/004093; Oct. 30, 2006; WIPO, 14 pgs.
"LDR Medical, by its attorneys; Terminal Disclaimer in Application Serial No. 13215123 Mar. 20, 2013", 2 pgs.
"Request for Continued Examination in U.S. Appl. No. 11/051,710, filed Jul. 11, 2013", LDR Medical, by its attorneys; USPTO; Alexandria, Virgina, 3 pgs.
"USPTO OA of Feb. 18, 2009 in U.S. Appl. No. 11/632,253", 14 pgs.
Bouduk, N, et al., "A biological basis for instantaneous centres of rotation of the vertebral column", Proc Institution Mechanical Engineers, (Jun. 16, 1995), 177-183.
Gertzban, S D, et al., "Centrode Patterns and Segmental Instability in Degenerative Disc Disease", BSc, M. Tile, MD, BSc, {Med), FRCS©, and B. Cruickshank, MD, FRCPath, Spine, vol. 10, No. 3 (Jan. 21, 1984), 257-261.
Griffith, S L, et al., "A Multicenter Retrospective Study of the Clinical Results of the Link SB Charite Intervertebral Prosthesis", vol. 19, No. 16, (Mar. 21, 1994), 1842-1849.
Haher, T R, et al., "Instantaneous Axis of Rotation as a Function of the Three Columns of the Spine", MS, Spine, vol. 17, No. 6, (Jan. 9, 1992), S149-S154.
Haher, T R, et al., "The Effect of the Three Columns of the Spine on the Instantaneous Axis of Rotation in Flexion and Extension", Spine, vol. 16, No. 8, (Apr. 16, 1991), S312-S318.
Klein, J A, et al., "Relocation of the Bending Axis During Flexion-Extension of Lumbar Intervertebral Discs and its Implications for Prolapse", Spine, vol. 8, No. 6, (Nov. 18, 1982), 659-664.
Kostuik, J P, "Alternatives to Spinal Fusion", vol. 29, No. 4, (Oct. 4, 1998), 701-715.
Liu, X, et al., "A New Technique for the Three-Dimensional Study of the Spine in Vitro and in Vivo by Using a Motion-Analysis System", Journal of Spinal Disorders, vol. 10, No. 4, (Jan. 30, 1997), 329-338.
Pearcy, M J, et al., "Instantaneous Axis of Rotation of the Lumbar Intervertebral Joints", vol. 13, No. 9, (Nov. 15, 1987), 1033-1041.
Seligman, S D, "Computer Analysis of Spinal Segment Motion in Degenerative Disc Disease With and Without Axial Loading", Spine, vol. 9., No. 6, (Dec. 31, 1983), 566-573.
White Ill, A A, et al., "Clinical Biomechanics of the Spine", 2nd Edition, J.B. Lippincott Co., (1990), 128-130.
Yoshioka, T, et al., "Motion Characteristics of the Normal Lumbar Spine in Young Adults: Instantaneous of Axis of Rotation and Vertebral Center Motion Analysis", Journal of Spinal Disorders, vol. 3, No. 2, (1990), 103-113.

\* cited by examiner

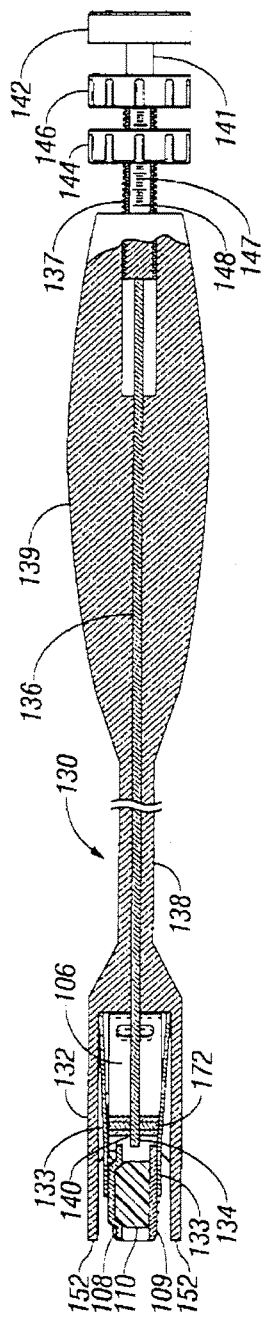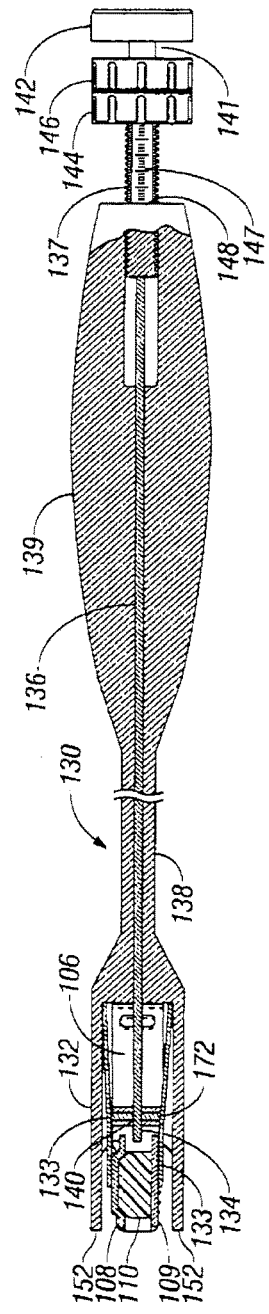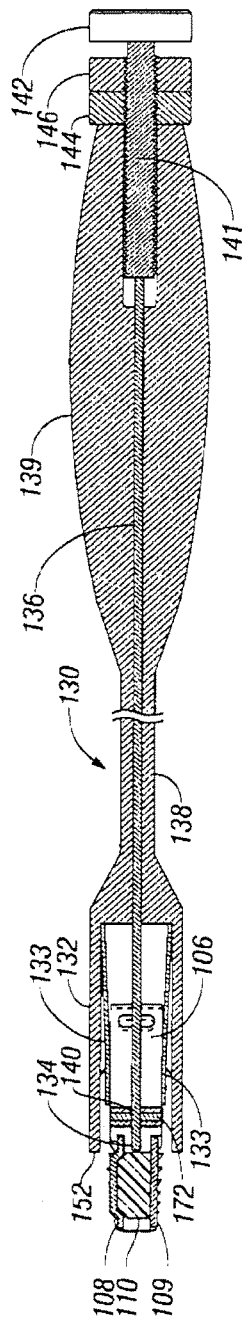
FIG. 6A
FIG. 6B
FIG. 6C

INTERVETERBRAL DISC PROSTHESIS INSERTION ASSEMBLIES

This application is a continuation of U.S. patent application Ser. No. 12/527,373 filed Mar. 19, 2010, now U.S. Pat. No. 8,685,100 issuing Apr. 1, 2014, which is a 35 U.S.C. § 371 application of PCT/IB2008/000349 filed Feb. 15, 2008, which claims priority to U.S. patent application Ser. No. 11/676,237 filed Feb. 16, 2007, now U.S. Pat. No. 8,465,546 issuing Jun. 18, 2013. All of the foregoing are hereby incorporated by reference.

TECHNICAL FIELD

This disclosure relates to the field of prostheses and in particular to intervertebral disc prostheses for replacement of natural intervertebral discs.

BACKGROUND

A healthy intervertebral disc is flexible enough to allow movement between adjacent vertebrae or between a vertebra and another adjacent spinal column element, such as the coccyx (the most inferior portion of the vertebral column, resulting from the fusion of the four coccygeal vertebrae) and the sacrum (a triangular bone that is the posterior skeletal element forming the pelvis, formed by 5 fused vertebrae). This movement accommodates bending of the spine. Disease or degeneration of the tissues of a natural intervertebral disc often leads to intense pain and reduced mobility. When degeneration or disease of the natural intervertebral disc has progressed to the point where non-operative care such as medication, injections, and/or physical therapy is ineffective, surgical intervention may be required.

A common procedure for treatment of degenerative or diseased intervertebral discs involves removal of the natural tissues of the disc and fusion of the adjacent vertebrae. Fusion eliminates the mobility between the adjacent vertebrae, however, and can transfer stresses and movements to the intervertebral discs above and/or below the point of fusion.

Intervertebral disc prostheses have been developed to mitigate some of the problems caused by intervertebral fusion. In particular, various designs of intervertebral disc prostheses can provide a relatively normal range of movement to the adjacent vertebra, resulting in a more normal distribution of stresses and movements along the various segments of the spine. Intervertebral disc prostheses typically are configured to restore normal disc height, and can decrease surgical morbidity and complications from post-operative immobilization instrumentation typically present in fusion procedures.

The patents FR 2 824 261, FR 2 846 550 and FR 2 865 629, and the patent application FR 2 893 838 (corresponding to applications WO 02/089701, WO 04/041129, WO 2005/074839 and WO 2007063398 and to U.S. patent application Ser. Nos. 10/476,565, 10/533,846, 11/051,710, and 11/362,253), each of which is assigned to the assignee of the present application and each of which is incorporated herein by reference for all purposes, disclose various intervertebral disc prosthesis configurations. In many of these configurations, the prosthesis may have an upper plate supporting the upper vertebra, a lower plate supporting the lower vertebra, and a mobile core or nucleus that provides some range of articulation between the upper plate and the lower plate.

Prior to the surgical implantation procedure, measurements often are made of the plates of the upper and lower vertebrae to confirm the viability of the procedure. Following discectomy in various representative procedures, the depth and width of the intervertebral space are measured, and a determination is made of an appropriate vertical spacing of the adjacent vertebra and the sizes of the upper and lower disc prosthesis plates and the core.

Typically, there are several selections for the depth and width of the intervertebral prosthesis plates and for the height of the core, depending on the type of intervertebral disc prosthesis. For example, the LDR Medical Mobi-C™ cervical disc prosthesis currently can be configured with any of 4 plate sizes and 3 core heights, and the LDR Medical Mobidisc™ lumbar disc prosthesis currently can be configured with any of 18 plate sizes and 6 core heights. In addition, the surgeon may wish to accommodate or correct a lordosis or kyphosis by using one or more plates having an angular offset between the vertebral axis implied by a normal to the plate's vertebral contact surface and a mean, or neutral, normal axis implied by the plate's core contact surface. Thus, even within a single product line, there may be numerous combinations of individual disc prosthesis elements available to suit the requirements of a particular patient. In various intervertebral prosthesis product systems, the upper plates, the lower plates, and the cores are provided to the sterile field of the surgical suite individually. Once the proper configuration of the upper plate, the lower plate, and the core has been determined, typically the surgical staff must acquire the proper upper plate, lower plate, and core from inventory.

The components of the prosthesis typically are then assembled for mounting with or loading into a prosthesis insertion tool, or assembled directly with the insertion tool, hi some systems, an assembly stand or jig is used for assembling the prosthesis components and loading the assembled prosthesis into an insertion tool. The selection and assembly process can be time consuming and awkward, potentially resulting in delays during the surgical proceeding. Handling of the components during assembly process can compromise the sterility of the prosthesis, and the use of additional handling equipment, such as an assembly stand or jig, can require further sterilization procedures, increase the complexity of the procedure, and clutter the surgical suite.

In some systems, an assortment of insertion tools are each configured for use with a single size or a limited range of sizes of the various prosthesis component combinations. Generally, the required size and configuration of the various prosthesis components will not be known until the surgical procedure has commenced. Thus, the surgeon will have to select the proper insertion tool during the procedure, following the determination of the proper sizes and configurations of the various prostheses components. The surgical staff therefore must disinfect and sterilize several insertion tools to have a full selection of the insertion tools at hand during the procedure. During the procedure, selection of the appropriate tool and confirmation of the selection will add to the duration and complexity of the surgical procedure. In various designs of insertion tools, however, the operative components of the insertion tool body are the same regardless of the prosthesis configuration, and only the tool's insertion adapter (for example, a head, holder, or other carrier of the assembled prosthesis) differs among the various insertion tools. Often, the differences among the various insertion adapters are dictated solely by the differences in sizes and configurations of the prosthesis components.

SUMMARY

In this context, one purpose of the present invention is to overcome the drawbacks of the prior art by proposing an intervertebral disc prosthesis delivery and insertion system which is easy to use and which can be provided in a stock which can be directly used during surgical procedures.

This purpose of the invention is reached by an intervertebral disc prosthesis delivery and insertion system comprising:
(a) a demountable insertion tool body; and
(b) plural intervertebral disc prosthesis insertion assemblies, each sterilized and packaged in sterile packaging to form a sterile pack and each comprising:
  (i) an insertion adapter having a coupler for the demountable insertion tool body and
  (ii) an intervertebral disc prosthesis releasably mounted to the insertion adapter.

According to another particular feature, the intervertebral disc prosthesis has a size and configuration specification.

According to another particular feature, the system further comprises an inventory storage space having storage locations for selected ones of the size and configuration specifications.

According to another particular feature, each sterile pack bears identifying information observable when the respective sterile pack is stored in the inventory storage space.

According to another particular feature, each storage location corresponds to one of the selected ones of the size and configuration specifications.

According to another particular feature, each of the intervertebral disc prostheses comprises:
  a first plate having a size and configuration selected from a set of first size and configuration specifications,
  a second plate having a size and configuration selected from a set of second size and configuration specifications, and
  a core having a size and configuration selected from a set of third size and configuration specifications.

According to another particular feature, the set of first size and configuration specifications is identical to the set of second size and configuration specifications.

According to another particular feature, one or more of the set of first size and configuration specifications, the set of second size and configuration specifications, and the set of third size and configuration specifications contains only one element.

According to another particular feature, the system further comprises an inventory storage space having storage locations for selected combinations of first size and configuration specifications, second size and configuration specifications, and third size and configuration specifications.

According to another particular feature, each primary sterile pack bears identifying information observable when the respective primary sterile pack is stored in the inventory storage space.

According to another particular feature, each storage location corresponds to one of the selected combinations of first size and configuration specifications, second size and configuration specifications, and third size and configuration specifications.

According to another particular feature, each storage location bears information observable when the location is empty, said information identifying the one of the selected combinations of first size and configuration specifications, second size and configuration specifications, and third size and configuration specifications to which such location corresponds.

Another purpose of the present invention is to overcome the drawbacks of the prior art by proposing Intervertebral Disc Prosthesis Insertion Assemblies which are easy to use and which can be provided in a stock which can be directly used during surgical procedures.

This purpose is reached by an intervertebral disc prosthesis insertion assembly comprising an insertion adapter having a coupler for a demountable insertion tool body and an intervertebral disc prosthesis releasably retained by the insertion adapter.

According to another particular feature, the insertion adapter and the intervertebral disc prosthesis are disposed in sterile packaging to form a sterile pack.

According to another particular feature, the insertion adapter has a surface complementary to and substantially fitting the intervertebral disc prosthesis.

According to another particular feature, the insertion adapter has at least one retainer that engages a recess and/or a post of the intervertebral disc prosthesis.

According to another particular feature, the retainer is a latch, and the recess is disposed on an edge of a plate of the intervertebral disc prosthesis.

According to another particular feature, the retainer is a dog, and the recess is disposed along a core of the intervertebral disc prosthesis.

According to another particular feature, the dog has a channel substantially matching the edge of a post of a plate of the intervertebral disc prosthesis.

Another purpose of the present invention is to overcome the drawbacks of the prior art by proposing packaged Intervertebral Disc Prosthesis Insertion Assemblies which are easy to use and which can be provided in a stock which can be directly used during surgical procedures.

This purpose is reached by a packaged intervertebral disc prosthesis insertion assembly comprising a sterile pack in which are disposed a sterile insertion adapter having a coupler for a detachable insertion tool body and components of a sterile intervertebral disc prosthesis.

According to another particular feature, the components of the intervertebral disc prosthesis are assembled and retained by the insertion adapter.

Another purpose of the present invention is to overcome the drawbacks of the prior art by proposing Intervertebral Disc Prosthesis Insertion Systems which are easy to use and which can be provided in a stock which can be directly used during surgical procedures.

This purpose is reached by an intervertebral disc prosthesis insertion system comprising:
  an insertion adapter having a coupler for a detachable insertion tool body; a detachable insertion tool body; and
  an intervertebral disc prosthesis releasably mounted to the insertion adapter.

According to another particular feature, the insertion adapter and the intervertebral disc prosthesis are disposed in sterile packaging to form a sterile pack.

According to another particular feature, the insertion tool body comprises an insertion actuator.

According to another particular feature, the insertion tool body comprises an insertion stop.

According to another particular feature, the insertion stop lock is adjustable.

According to another particular feature, the insertion tool body comprises an insertion stop lock.

Another purpose of the present invention is to overcome the drawbacks of the prior art by proposing methods for Intervertebral Disc Prosthesis Insertion which are easy to use and which can be provided in a stock which can be directly used during surgical procedures.

This purpose is reached a method of inserting an intervertebral disc prosthesis between adjacent elements of a spinal column, the method comprising the steps of:

providing an insertion adapter and an intervertebral disc prosthesis;

mounting the intervertebral disc prosthesis to the insertion adapter to form an insertion assembly;

providing an insertion tool body;

mounting the insertion assembly to the insertion tool body; inserting the intervertebral disc prosthesis between adjacent elements of a spinal column; and demounting the intervertebral disc prosthesis from the insertion assembly.

According to another particular feature, the method further comprises the step of demounting the insertion adapter from the insertion tool body and discarding the insertion adapter.

This purpose is also reached by a method of inserting an intervertebral disc prosthesis between adjacent elements of a spinal column, the method comprising the steps of:

providing an insertion adapter and components of an intervertebral disc prosthesis; assembling the components of the intervertebral disc prosthesis and the insertion adapter to form an insertion assembly; providing an insertion tool body;

assembling the insertion assembly and the insertion tool body; placing the intervertebral disc prosthesis between adjacent elements of a spinal column; and removing the intervertebral disc prosthesis from the insertion assembly.

According to another particular feature, the step of providing an insertion adapter and components of an intervertebral disc prosthesis comprises the steps of:

packaging the components of the intervertebral disc prosthesis and the insertion adapter in sterile packaging to form a sterile pack; and then transporting the sterile pack to a sterile field.

According to another particular feature, the method further comprises the steps of:

packaging the insertion assembly in sterile packaging to form a sterile pack; and then transporting the sterile pack to a sterile field.

This purpose is also reached by a method of aseptically delivering an intervertebral disc prosthesis insertion assembly to a sterile field, the method comprising the steps of:

providing sterile components of an intervertebral disc prosthesis and a sterile insertion adapter having a coupler for a detachable insertion tool body;

packaging the components of the intervertebral disc prosthesis and the insertion adapter into sterile packaging to form a primary sterile pack;

transporting the sterile pack containing the intervertebral disc prosthesis and the insertion adapter into a sterile field; and removing the intervertebral disc prosthesis and the insertion adapter from the sterile pack within the sterile field.

According to another particular feature, the method further comprises, prior to the step of packaging, the step of assembling the components of the intervertebral disc prosthesis and the insertion adapter.

According to another particular feature, the method further comprises the step of packaging the primary sterile pack into a secondary sterile pack.

Another purpose of the present invention is to overcome the drawbacks of the prior art by proposing packaged Intervertebral Disc Prosthesis Insertion Assemblies which are easy to use and which can be provided in a stock which can be directly used during surgical procedures.

This purpose is reached by a packaged intervertebral disc prosthesis insertion assembly comprising a sterile pack in which are disposed a sterile insertion tool and sterile components of an intervertebral disc prosthesis.

According to another particular feature, the components of the intervertebral disc prosthesis are assembled with the sterile insertion tool.

Another purpose of the present invention is to overcome the drawbacks of the prior art by proposing Intervertebral Disc Prosthesis Insertion Systems which are easy to use and which can be provided in a stock which can be directly used during surgical procedures.

This purpose is reached by an intervertebral disc prosthesis delivery and insertion system comprising plural packaged intervertebral disc prosthesis insertion assemblies, each of the packaged intervertebral disc prosthesis insertion assemblies comprising a sterile insertion tool and sterile components of an intervertebral disc prosthesis packaged in sterile packaging to form a primary sterile pack.

According to another particular feature, each of the intervertebral disc prostheses has a size and configuration specification.

According to another particular feature, the system further comprises an inventory storage space having storage locations for selected ones of the size and configuration specifications.

According to another particular feature, each primary sterile pack bears identifying information observable when the respective primary sterile pack is stored in the inventory storage space.

According to another particular feature, each storage location corresponds to one of the selected ones of the size and configuration specifications.

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various embodiments, the prosthesis and an insertion tool are provided in a sterile pack, with the prosthesis components and the insertion holder sterilized and packaged in one or more types or layers of sterile packaging. Intervertebral disc prosthesis insertion assemblies, intervertebral disc prosthesis insertion systems, intervertebral disc prosthesis delivery and insertion systems, methods of inserting an intervertebral disc prosthesis between adjacent elements of a spinal column, methods of inserting an intervertebral disc prosthesis between adjacent elements of a spinal column, and methods of aseptically delivering an intervertebral disc prosthesis insertion assembly to a sterile field are also disclosed.

BRIEF DESCRIPTION OF THE SEVERAL VIEWS OF THE DRAWINGS

Other features and advantages of various embodiments and various aspects of the present invention will appear more clearly to those of skill in the art on reading the description that follows, with reference to the appended drawings in which:

FIGS. 6A, 6B, and 6C depict various views of an embodiment of an insertion tool body.

DETAILED DESCRIPTION OF VARIOUS EMBODIMENTS

Figure 1:
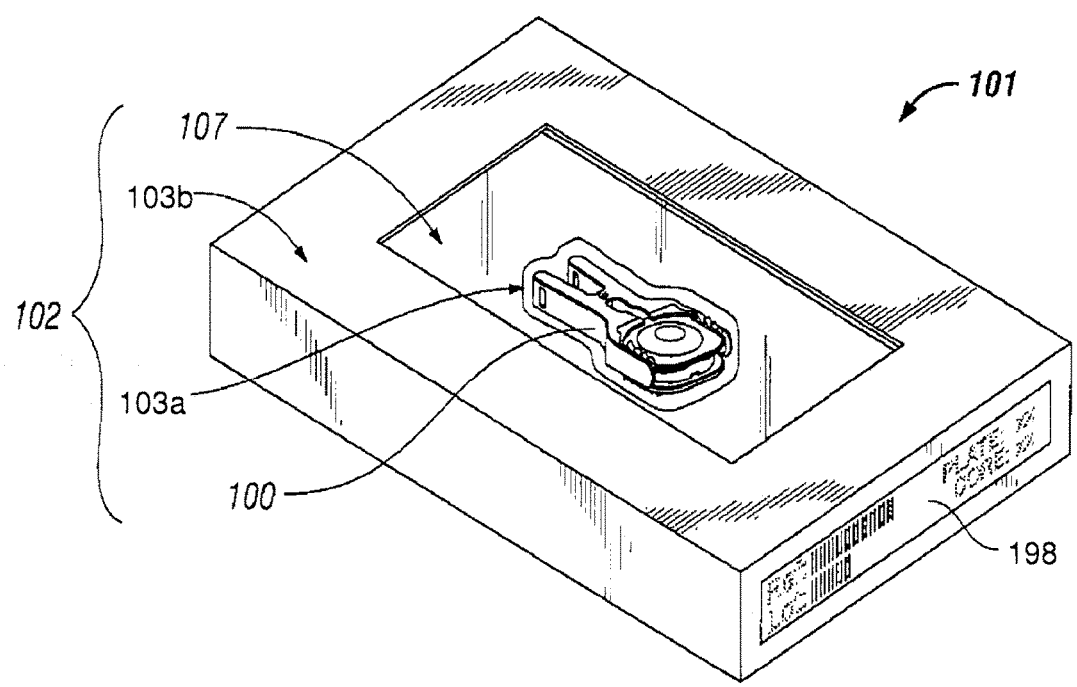
FIG. 1 depicts an embodiment of a sterile pack comprising a prosthesis insertion assembly.
Figure 2:
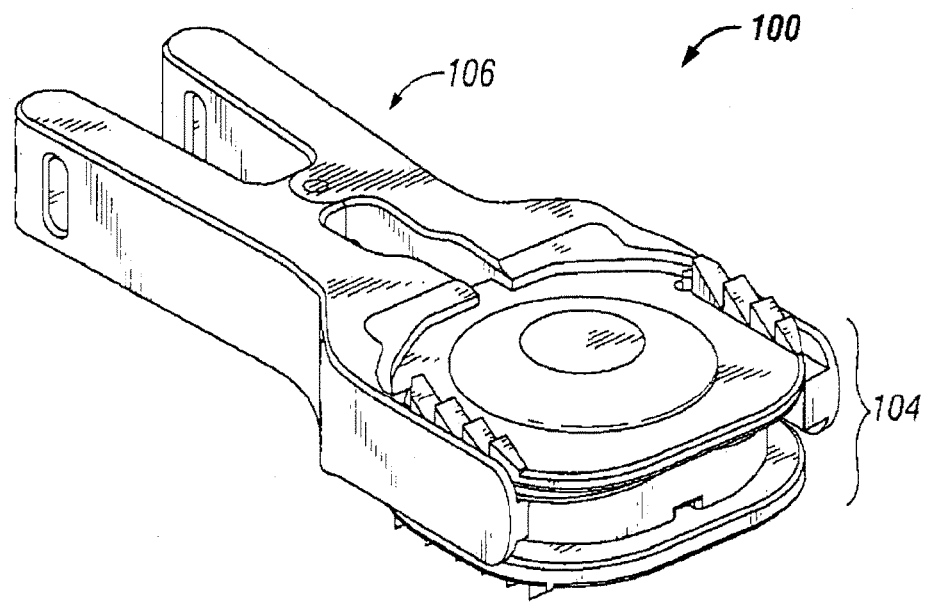
FIG. 2 depicts an embodiment of a prosthesis insertion assembly.

In several embodiments of the invention, the prosthesis insertion assembly is arranged so that it is possible that the prosthesis is never directly touched during the insertion procedure. This arrangement is particularly advantageous in that it limits or prevents the risks of contamination of the prosthesis during the insertion procedure. Various embodiments of a sterile package or sterile prosthesis insertion assembly are provided to facilitate the insertion of the prosthesis between adjacent vertebrae and so that the surgeon can use an assembly for the insertion of the prosthesis without having any direct contact with the prosthesis. FIG. 1 depicts one of many possible embodiment of a packaged intervertebral disc prosthesis insertion assembly (101). In this embodiment, a sterile insertion adapter (106) and sterile components of an intervertebral disc prosthesis (104) may be assembled together to form a sterile prosthesis insertion assembly (100) as shown in FIG. 2, which is disposed in primary, or inner, sterile packaging (103a) and in secondary, or outer, sterile packaging (103b) to form a sterile pack (102). The components of the intervertebral disc prosthesis (104) may be assembled with the insertion adapter (106) and provided to the sterile field of a surgical suite pre-configured and ready to use. It will be understood that the configurations of a primary (103a) and secondary (103b) packaging to form a sterile pack (102, 202) are arbitrary and that the invention can be used with other configurations of packaging, such as, for example, a sterile pack (102, 202) comprising only one layer, two layer (as in the above example when considering that the primary and secondary package are layers) or more than two layers, each layer possibly being different one of another. The various elements forming the assemblies explained below can be packed in such packaging, assembled or not, with a preference of at least all the component of the prosthesis being assembled, for example mounted to an adapter, for example held by an insertion tool. With such configurations, the sterile pack will be delivered to the sterile field for implantation onto a patient and the components of the prosthesis will not be touched during the insertion procedure, thus limiting the risks of contamination.

FIG. 2 depicts one of many potential embodiments of an insertion assembly (100). Various embodiments of the insertion assembly (100) may comprise an intervertebral disc prosthesis (104) and an insertion adapter (106), which holds the prosthesis (104) and couples with, mounts to, or otherwise joins or engages a detachable or demountable surgical tool body (130), for example as illustrated in FIG. 4, used in implanting the prosthesis (104). The prosthesis (104) can be of the type manufactured by LDR Medical, described herein or in the patents FR 2 824 261, FR 2 846 550, FR 2 865 629, FR 2 869 528, FR 2 879 436 (corresponding, respectively to applications WO 02/089701, WO 04/041129, WO 2005/074839, WO 2005/104996 and WO 2006/120505), or in applications FR 2 891 135 and FR 2 893 838 (corresponding, respectively to applications WO 2007/034310 and WO 2007063398), filed by the applicant of the present application (or corresponding US applications assigned to the assignee of the present application). Such prostheses can comprise, for example, at least a first plate, a second plate and a core mobile in rotation and/or in translation in relation to at least one of the plate, with arrangements for cooperation of the core and at least one of the plates, so as to limit or prevent the movements of the core in relation to at least one of the plates. The invention can also comprise a prosthesis of another type, for example as known from prior art and possibly including the various arrangements necessary for its use in the assembly as described below. In the embodiment of FIG. 4, a clip (126), for example as illustrated in FIG. 3, provides additional restraint to the components of prosthesis (104).

Figure 3:
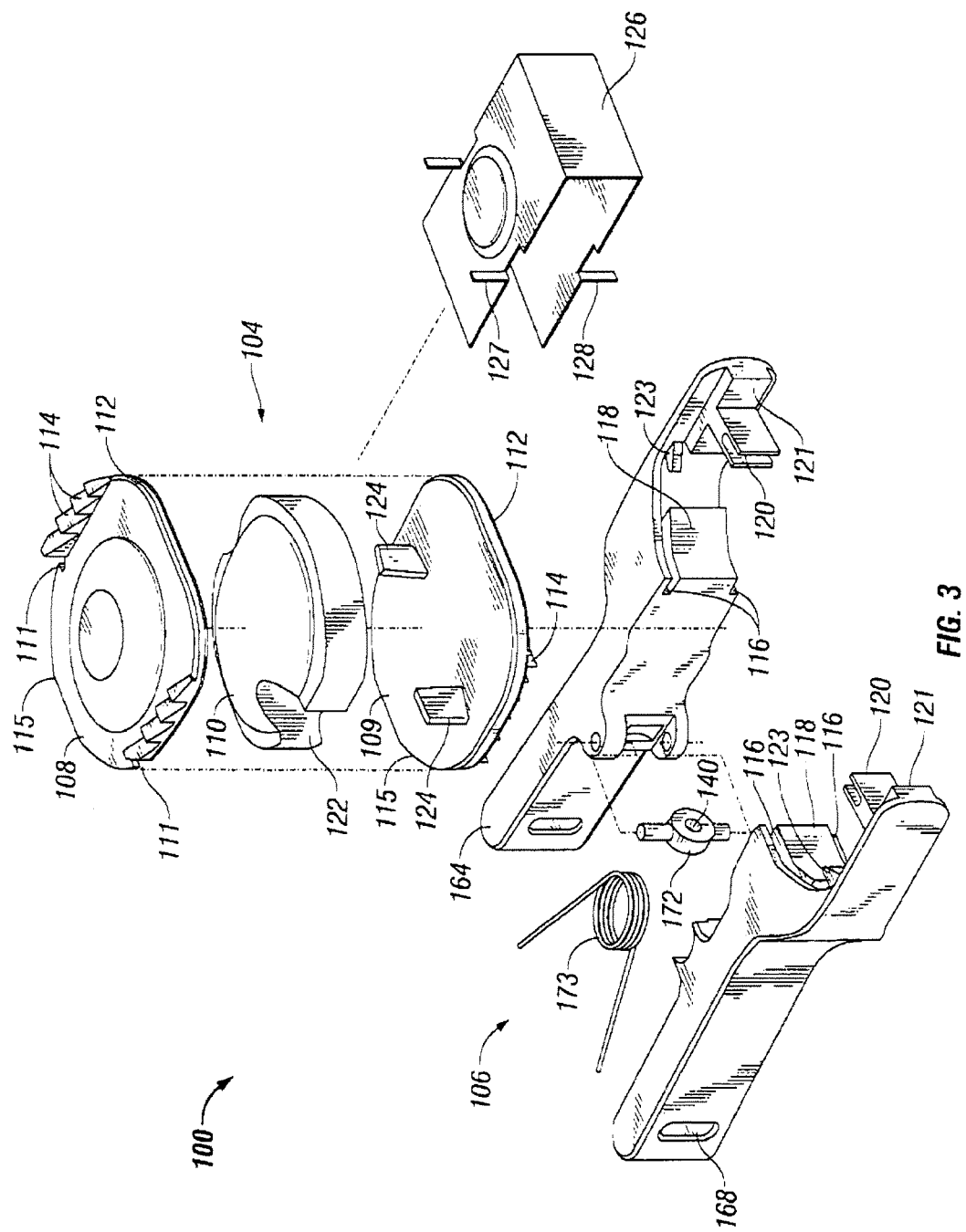
FIG. 3 depicts details of an embodiment of a prosthesis insertion assembly.
Figure 4:
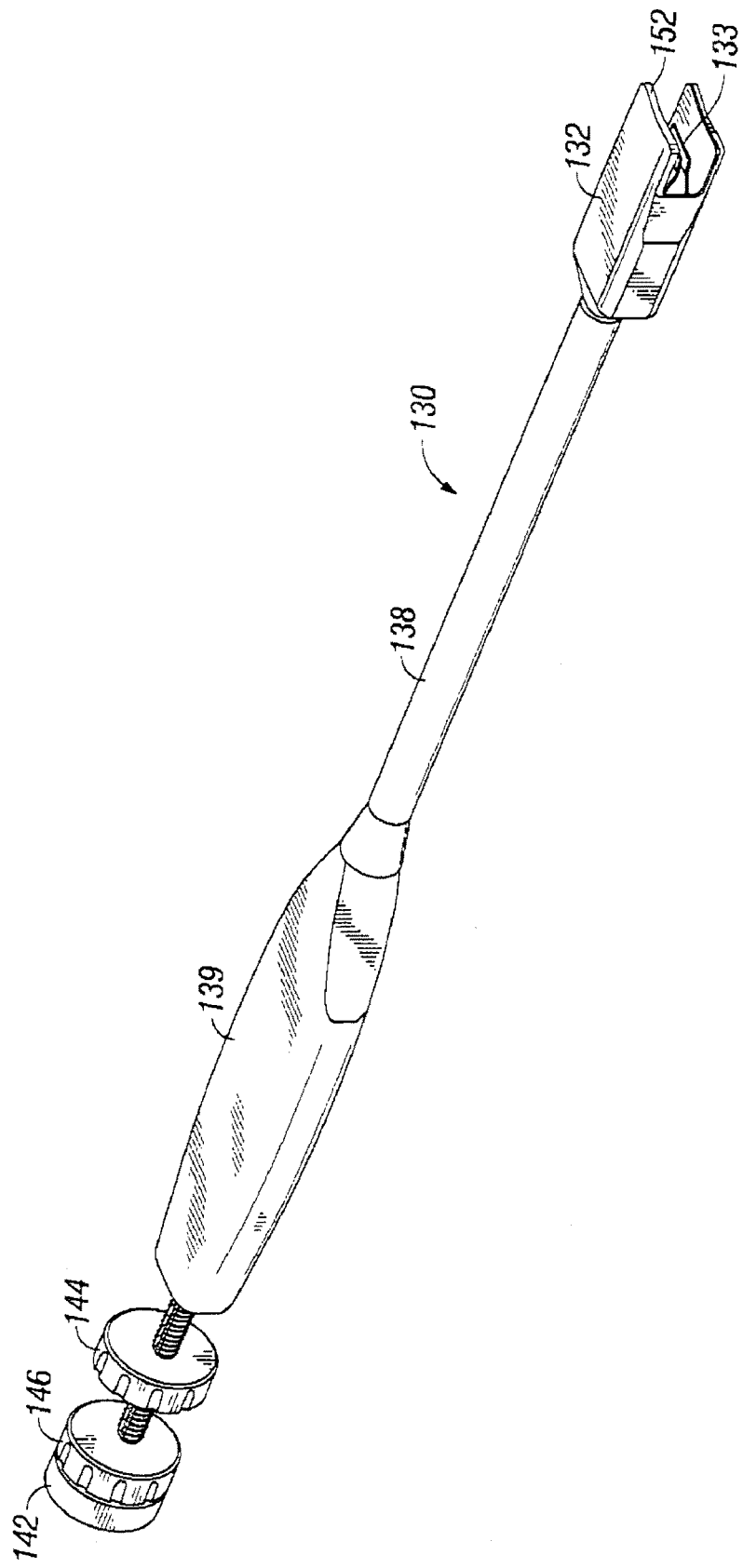
FIG. 4 depicts an embodiment of an insertion tool body.

FIG. 3 shows an exploded view of an embodiment of a prosthesis (104) and an insertion adapter (106). The prosthesis (104) in this embodiment comprises a first plate, such as upper plate (108), a second plate, such as lower plate (109), and a mobile core (110). The configurations of "upper" and "lower" plates generally are reversible, and the designation of the plates as "first plate" and "second plate" or as "upper plate" and "lower plate", of course, is purely arbitrary. The upper and lower plates (108, 109) preferably may be made of chromium, cobalt, and molybdenum, but other compositions may used. In various preferred embodiments, the core may be made of an ultrahigh molecular weight polyethylene but other compositions can be used. A titanium and hydroxyapatite plasma spray coating may optionally be applied to the vertebral contact surfaces of the upper and lower plates (108, 109) to encourage at least partial fusion with the adjacent vertebrae by bony ingrowth or other forms of adhesion. The prosthesis (104) in various embodiments may contain other features. For example, second plate (109) maybe configured with core-travel stops, for example posts (124) as illustrated, that limit the translational and rotational movement of core (110). In such embodiments, contact between the stops (124) and the recesses (122) along the perimeter of the core body may be configured to limit the translational and rotational movement of the core (110). The plates (108, 109) optionally may have angled edges (115) configured for complementary contact with optional angled contact surfaces (116) of the insertion adapter (106), the benefits of which are described in greater detail below.

Additional optional features of the prosthesis (104) may facilitate implantation of the prosthesis and its stability once implanted. For example, one or more of the edges of the prosthesis (104) that encounter the surfaces of the vertebrae (150) during prosthesis insertion may be beveled, for example edges (112) of the upper plate (108) and the lower plate (109), which may reduce the effort required to insert the prosthesis (104). Alternate embodiments may not contain this bevel at all, or may be beveled in only a few strategic locations around the perimeter of the plates (108, 109). Various embodiments also may have anchors (114) that, for example, may comprise notches or teeth disposed on either or both of the plates (108, 109) in the region of one or more edges of the prosthesis (104), or one or more anchors may be elsewhere along either or both of the vertebral contact surfaces of the plates (108, 109). The anchors (114) may be configured in such a way that they minimize the force required during the implantation of the prosthesis (104), while opposing subsequent movement of the prosthesis. After the prosthesis (104) is implanted, anchors (114) preferably stabilize the prosthesis (104) and oppose movement relative to the vertebrae (150) in multiple ways. For example, the anchors (114) may provide teeth opposing movement, primarily in the direction of removal, between the prosthesis (104) and the vertebrae (150), thus helping to keep the prosthesis (104) in place after implantation and during withdrawal of the insertion adapter (106). The surfaces of the plates (108, 109) also may have a porous biocompatible coating, for example as described above, that also allows adhesion of the osseous tissue and its fusion with the prosthesis. Once osseous tissue has adhered to the plates (108, 109) and grown around the anchors (114), a strong connection may be formed between each of the plates (108, 109) of the prosthesis (104) and the respective adjacent vertebra (150). In alternate embodiments, the porous, biocompatible coating may be replaced or supplemented with a porous, bioactive coating, which may stimulate the formation of osseous tissue, and/or with an antiseptic coating, which may deter or counteract infection at the surface of the implant.

After discectomy (whether complete or partial) and distraction of adjacent elements of a spinal column such as vertebrae (150), prosthesis implantation surgical procedures may involve measurements of intervertebral disc space. These measurements may be used to determine the dimensions and configurations of the upper plate (108), the lower plate (109), and the mobile core (110) to be implanted. In various embodiments, the prosthesis (104) generally may be configured to assist in the correction of various types of spinal disorders, including lordosis and kyphosis. Correction of lordosis or kyphosis may involve imposition of an angle, for example between 0 and 15 degrees, between the upper plate (108) and the lower plate (109) in the postero-anterior direction. The upper plate (108), the lower plate (109), or the core (110) may be configured to assist in imposing such an angle, for example as discussed in Patent FR 2 824 261 assigned to the assignee of the present application. Such angle can be imposed between the upper plate and the lower plate thanks to a core or nucleus having its upper and lower surface imposing an angle (one surface of the core being inclined with respect to the other) or by having at least one of the plate having its upper and lower surface imposing an angle (one surface of at least one of the plate being inclined with respect to the other surface of this plate). In addition, the plates (108, 109) and the core (110) generally have dimensions and configurations selected for the particular patient in which the prosthesis (104) will be implanted. Often, in practice the dimensions and configurations of the prosthesis (104) will not be known until well into the surgical procedure. Accordingly, for any particular patient the surgical staff will need an assortment of prosthesis insertion assembly configurations on hand.

Figure 22A:
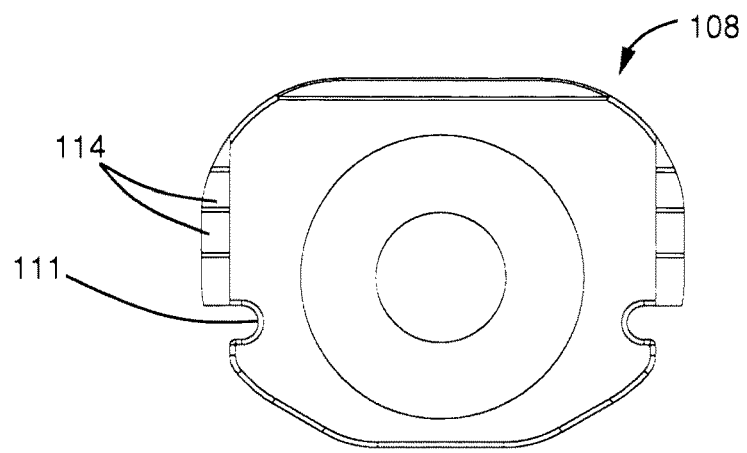
FIGS. 22A, 22B and 22C depict, respectively, an elevation view of a first plate of an intervertebral disc prosthesis, a side view of a second plate of an intervertebral disc prosthesis and an elevation view of the second plate of an intervertebral disc prosthesis, according to various embodiments.
Figure 22B:
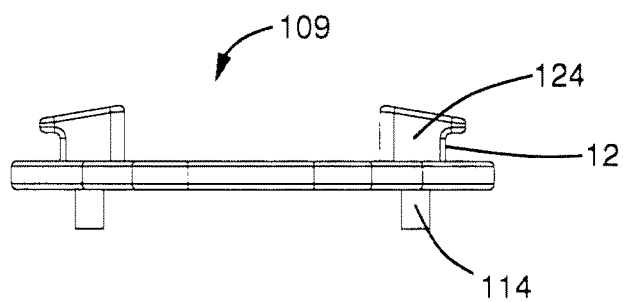
Figure 22C:
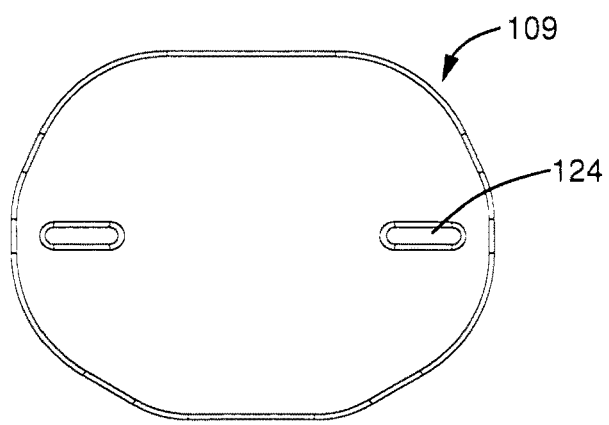

In various embodiments, the plates (108, 109) and core (110) of the prosthesis (104) may be retained by or releasably mounted to an insertion adapter (106). The insertion adapter (106) may be configured in many ways, such as a head, holder, or other carrier of an assembled prosthesis (104), for example. The insertion adapter (106) optionally may have jaws (121) that hold the prosthesis by grasping or pinching the lateral edges of the upper and lower plates of the prosthesis. The insertion adapter (106) may further comprise one or more optional retainers, such as mounting dogs (120). The dogs (120) may engage a respective recess (122) located in the mobile core (110) and contact or grasp a respective one of the posts (124) located on the lower plate (109). The dogs (120) may have surfaces configured to substantially match the spacing and/or configuration of the faces of the recesses (122). One or more of the dogs (120) may be equipped with a channel substantially matching the edge of one of the respective posts (124), to increase the effectiveness of the grasp on the lower plate (109). In addition, the insertion adapter (106) may optionally have additional retaining, grasping, or securing means, for example the illustrated latches (123) disposed on jaws (121), which may engage complementary retaining, grasping, or securing means, such as a receiver, recess, notch, etc., for example the recesses (111) disposed along opposite lateral edges of plate (108). For example, FIG. 22A depict an example of recess (111) enabling to an upper plate (108) to be held by an insertion adapter (106, not shown on this figure), for example thanks to latches (123), and FIG. 22B depict an example of a post (124) (shaft, jamb, stud or pillar) of a lower plate (109), enabling to this plate to be held and comprising a shoulder (12) intended to cooperate with dogs (120) of an insertion adapter (106), so as to maintain the prosthesis and avoid the prosthesis to fall when held by the adapter (106), for example of a type detailed later in reference to FIGS. 18(A to C). It will be understood, when reading the present description, that the various embodiments of the holder and adapter can be envisaged, with or without a supplementary clip (126) for holding the prosthesis.

The insertion adapter (106) in various embodiments also may comprise angled contact surfaces (116) configured for complementary contact with optional angled edges (115) of the prosthesis plates (108, 109). An optional shoulder (118) may be configured for complementary contact with the perimeter of the core (110). The combined height of the contact surfaces (116) and the shoulder (118) may preferably be substantially equal to the distance between the plates (108, 109) of an assembled prosthesis (104). The contact surfaces (116) and the shoulder (118) in various embodiments thus may combine to provide a surface of the insertion adapter (106) complementary to, and substantially fitting, the prosthesis (104) when assembled with, or mounted or attached to, the insertion adapter (106). A complementary fit between angled structures such as this may help stabilize the prosthesis (104) and push its components uniformly into the intervertebral disc space, preventing unwanted rotation or transverse movements of the prosthesis (104) or its components during insertion.

Various embodiments may incorporate any or all of the structures discussed above, but may also have other attachment and support mechanisms. For example, some embodiments optionally may have additional mount points, such as in the upper plate (108), the lower plate (109), or both. Other alternative embodiments could have retainers such as pins or clips that fit into one or more cavities or recesses of various prosthesis components, or one or more of many other methods that could be used to grasp objects and allow for convenient release when desired.

The insertion adapter (106) in various embodiments may have actuator means for releasing the intervertebral this prosthesis (104). In various embodiments, the actuator may be configured as spring-loaded arms, tangs, shanks, or other actuating means (164) articulable about articulating means such as a hinge pin (172). Alternatively, the insertion adapter (106) may have an integral hinge portion about which the arms, tangs, shanks, or other actuating means (164) articulate, for example comprising a flexible material such as plastic or rubber or stress/strain relief features such as cuts or voids.

In some embodiments of the invention, the insertion adapter (106) can comprise a body split in at least two parts (164), complementary one with another and assembled so as to hold at least part of the prosthesis (104), at least at an end of the adapter (106) comprising dogs (120) or latches (123). These dogs or latches (120, 123) can, in some embodiments, be formed by branches prolonging a lateral surface of each of the parts (164) of the adapter's body. The term "dogs" shouldn't be construed restrictively since the arrangement can be formed by branches having a shape adapted to hold the prosthesis at an end of the branch, as detailed below. Preferably, the adapter (106), in these embodiments, will be split along its longitudinal axis (i.e., the axis of insertion of the prosthesis) so that the 2 parts of its body surround and hold the prosthesis on the lateral faces of the latter. Thus, in these embodiments, the actuating means (164) of the adapter (106) are formed by the assembly of the 2 parts of the body, for example thanks to a pin (165a) penetrating in a channel (165e) or hole, such as a drilling for example, passing through, at least partially, each of the parts (264) of the body of the insertion adapter (106). FIGS. 18(A to C), 19 (A and B), 20(A to C), 21 (A and B), 23(A to C) and 24(A and B), show several, illustrative but not limitative, examples of the possible embodiments and FIGS. 25(A and B) and 26 (A to D) show examples of embodiments of a sterile insertion tool (131), particularly adapted to these embodiments of the insertion adapter (106). In these embodiments, actuating the insertion adapter (106) for releasing the prosthesis (104) will be performed by withdrawing the pin (165a) and by disassembling the two parts (164) of the body of the insertion adapter (106) forming the actuating means (164), as detailed hereafter. These embodiments of the insertion adapter (106) can also be pre-assembled with the prosthesis (104) in a sterile package, eventually with the sterile insertion tool (131).

Figure 18A:
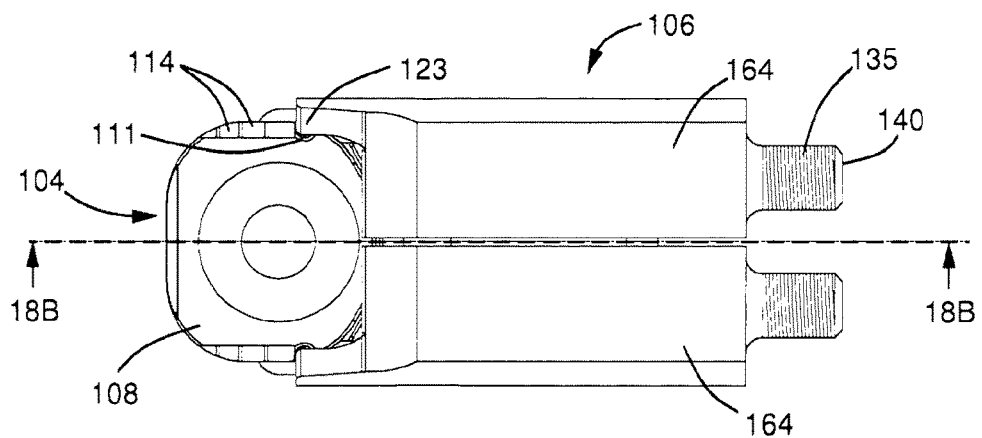
FIGS. 18A, 18B and 18C depict, respectively, an elevation view, a cross section view along cut plane (18B-18B) of FIG. 18A and a cross section view along cut plane (18C-18C) of FIG. 18B, of an embodiment of a prosthesis insertion assembly.
Figure 18B:
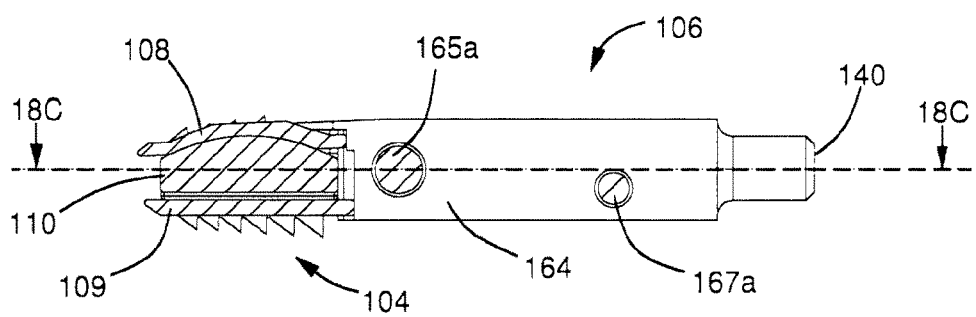
Figure 18C:
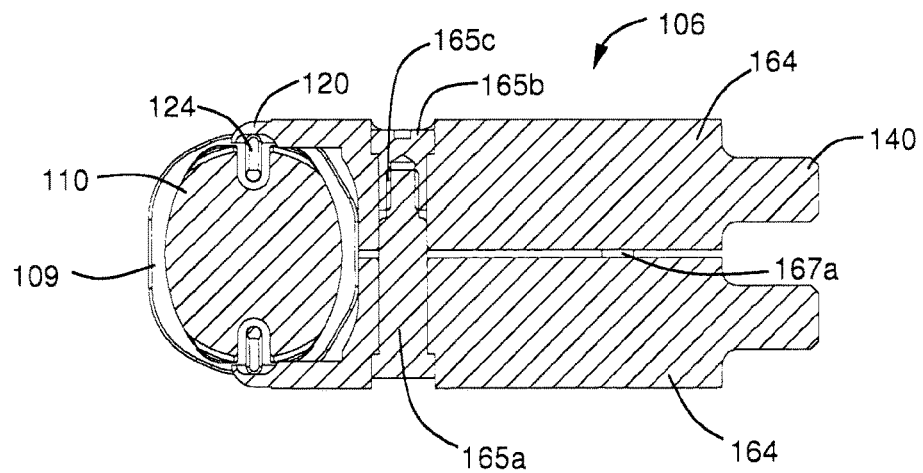
Figure 19A:
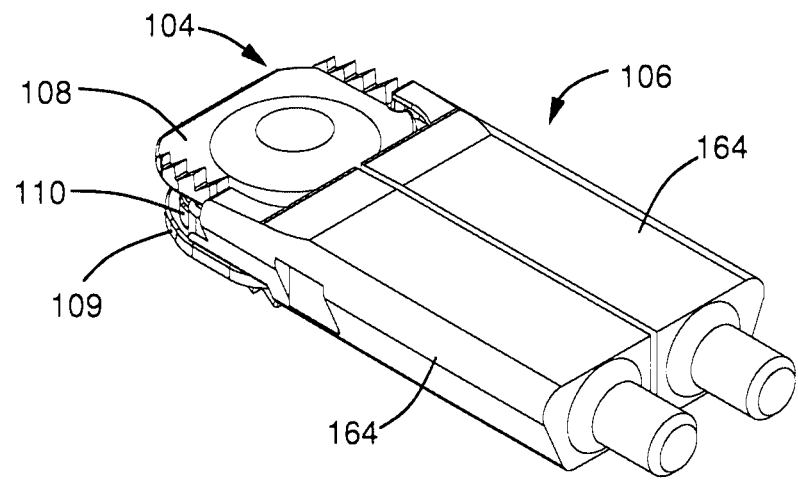
FIGS. 19A and 19B depict perspective views of an embodiment of a prosthesis insertion assembly, respectively assembled and disassembled.
Figure 19B:
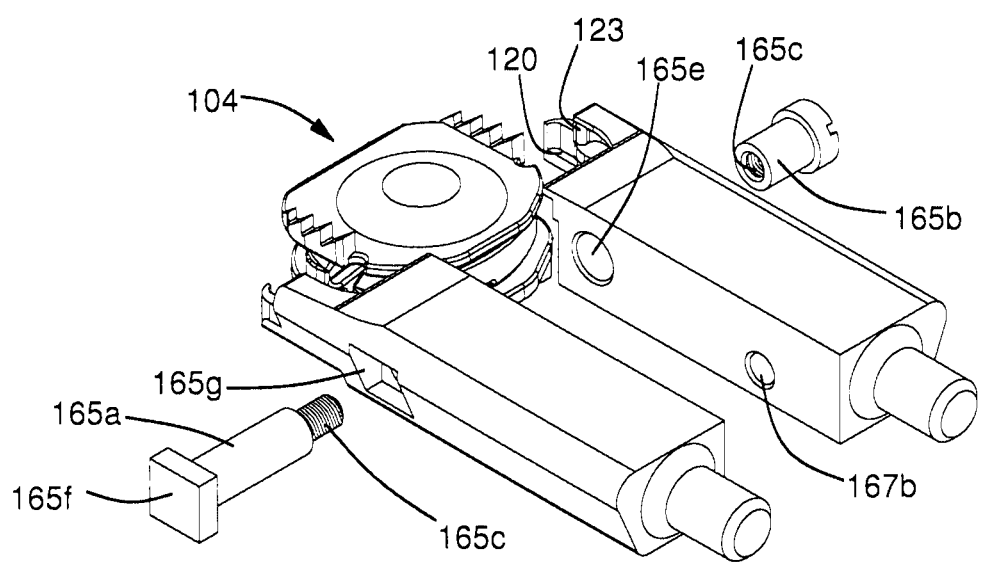

FIG. 18A show an embodiment of the insertion adapter (106) holding a prosthesis (104) in particular thanks to the cooperation between the latches (123) of the adapter and the recesses (111) of the upper plate (108) of the prosthesis (104), forming a mechanism for locking the prosthesis (104) on the adapter (106). The two parts (164) of the body of the adapter (106) have a substantially parallelepiped shape in this example shown on FIGS. 18(A to C), except at the end equipped with the dogs and latches for holding the prosthesis. Thus, the two parts (164) of the body, split along the longitudinal axis of the body, are assembled around the prosthesis and cooperate, in this example, through a substantially flat surface. The two parts (164) of the body of the adapter (106) are equipped with a coupler (140) enabling the adapter (106) to be mounted on an insertion tool (131, FIGS. 25A and 25B, for example). It should be noted that several variants of implementation comprising only one coupler on only one of the two parts of the body of the adapter can be envisaged. In the example shown, this coupler (140) comprises a shank intended to cooperate an actuator (136, FIG. 25B), such as a rod for example, provided with a threaded hole (134) for its screwing onto the coupler (140). It will be noted that the configuration of the shank (threaded rod) of the coupler (140) and the threaded hole (134, FIG. 26B) of the actuator (136) of the insertion tool (131) can of course be inversed or be replaced by other arrangements for coupling (holding, fixing) the adapter (106) and the insertion tool (131). Thus, for example, the coupler of the adapter can comprise a threaded hole (140) cooperating with a threaded end (134) of the actuator (136) of the insertion tool. In other embodiments, the coupler (140) can comprise a rod provided with a flat (165d) intended to cooperate with a duct comprising a shoulder, at an end of the actuator (136, FIG. 25B). In other embodiments, the coupler (140) can comprise a rod, threaded and comprising a flat (165d), so that the adapter (106) and/or the pin (165a) (in the case where it is the pin (165a) which holds the coupler (140) as detailed hereafter) can be manipulated both by a tool comprising a shoulder cooperating with the flat and by a tool comprising a threaded hole. Furthermore, other embodiments envisaged comprise a coupler having a threaded hole at the bottom of which a shoulder is arranged, such coupler thus being capable to cooperate both with a threaded end (134) of an actuator (136, FIG. 25B) and with a tool comprising a rod having a flat at one end. FIG. 18B show a cross section of such embodiment, with the angled edges (115) of the plates (108, 109) of the prosthesis abutting the angled surfaces or edges of the adapter (106). In some embodiments (not shown), the adapter (106) also comprises a shoulder or a surface for contact with the core (110) for maintaining the various elements (108, 109, 110) of the prosthesis in a position suited for the insertion between vertebrae. As particularly visible on FIG. 18C, the assembly of the two parts (164) of the body of the adapter (106) is performed in this example by at least one pin (165a) transversally passing through the adapter (106), from side to side, in the horizontal plane. In this example, the pin (165a) is provided with a threaded end (165c) enabling its screwing in a threaded hole of a swivel (or any other arrangement for assembling). The screwing of the pin (165a) and the swivel (165b) allows maintaining together the two parts (164) of the body of the adapter which maintain (hold, surround) the elements of the prosthesis, in particular thanks to the dogs (120) cooperating with the post (124) of the lower plate (109) of the prosthesis and eventually to the latches (or dogs) (123) cooperating with the recesses (11) mentioned previously. In the example depicted in FIG. 18C, the assembly of the two parts (164) of the adapter's (106) body is strengthened by a rod (167a) protruding from one of the two parts (164) and penetrating in a hole (167b, FIG. 19b) of the other part. However, this strengthening (167a, 167b) of the assembly is not critical and some embodiments only comprise the pin (165a). As particularly visible on FIG. 19B, the pin (165a) can comprise, in some embodiments, a stop (165f) cooperating with a housing (165g) of complementary shape, arranged in one of the two parts (164) of the adapter's (106) body, so as to oppose to the rotation of the pin (165a) during the screwing of the swivel (165b). Thus, the adapter's assembly can simply be performed by inserting the pin (165a) into a hole (165e) passing through the two parts (164) of the body and by the screwing of the threaded hole (165c) of the swivel (165b) onto the threaded end (165c) of the pin (165a). It should be noted that the term "swivel" is used herein to designate an element which can be screwed on a threaded rod but any similar structure can be used, for example the one shown in FIG. 19B and comprising a slit allowing the screwing with a screwdriver. Furthermore, instead of a swivel, a threaded hole disposed directly in one of the two parts (164) allows the screwing of a threaded pin (165a) without requiring other structures. Similarly, the configuration of the threadings can be inversed or replaced by any other arrangement for fixing the pin. It should be noted that, in the example shown on FIG. 19B, the dogs (123, 120) intended to maintain the plates are provided with a shoulder forming an horizontal surface supporting each plate, so that the prosthesis is maintained without requiring too much pressure on the recesses (111) and posts (124) of the plates.

Figure 20A:
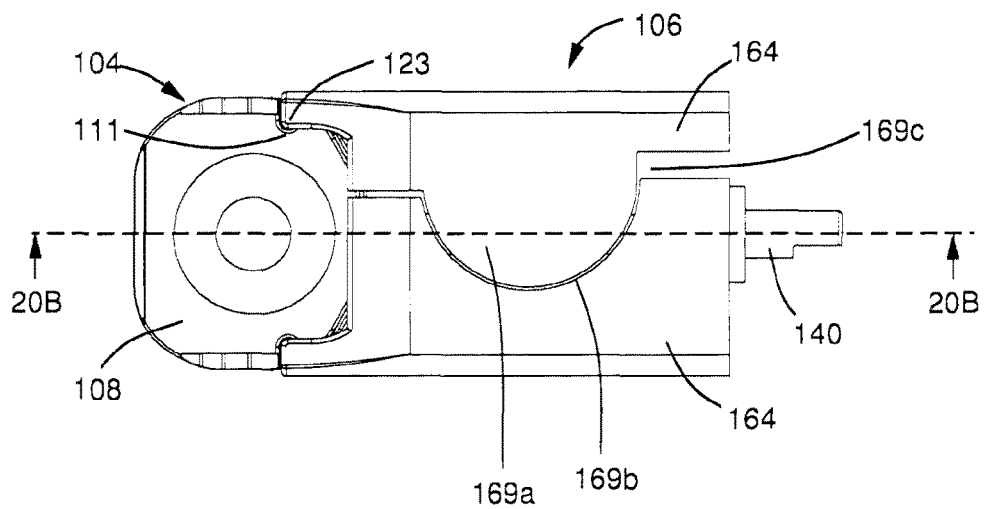
FIGS. 20A, 20B and 20C depict, respectively, an elevation view, a cross section view along cut plane (20B-20B) of FIG. 20A and a cross section view along cut plane (20C-20C) of FIG. 20B, of an embodiment of a prosthesis insertion assembly.
Figure 20B:
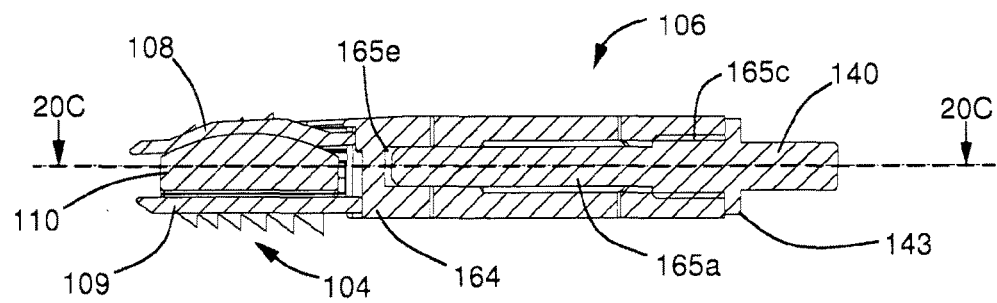
Figure 20C:
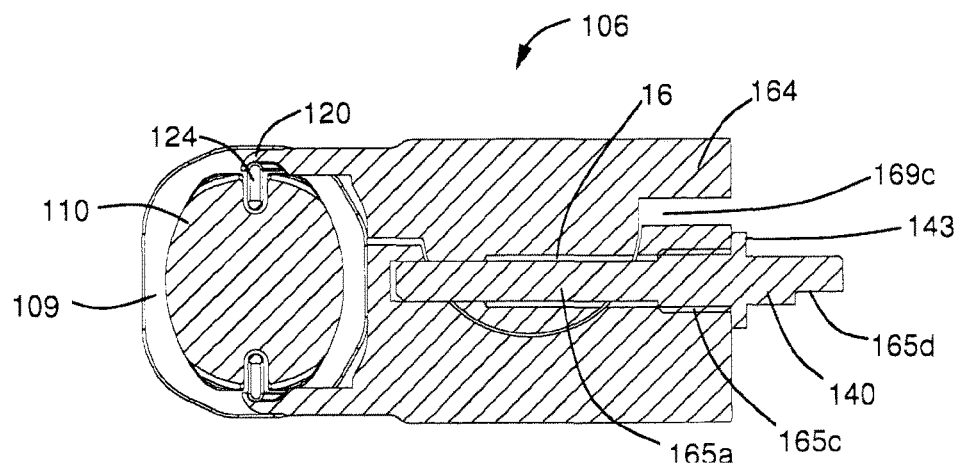
Figure 21A:
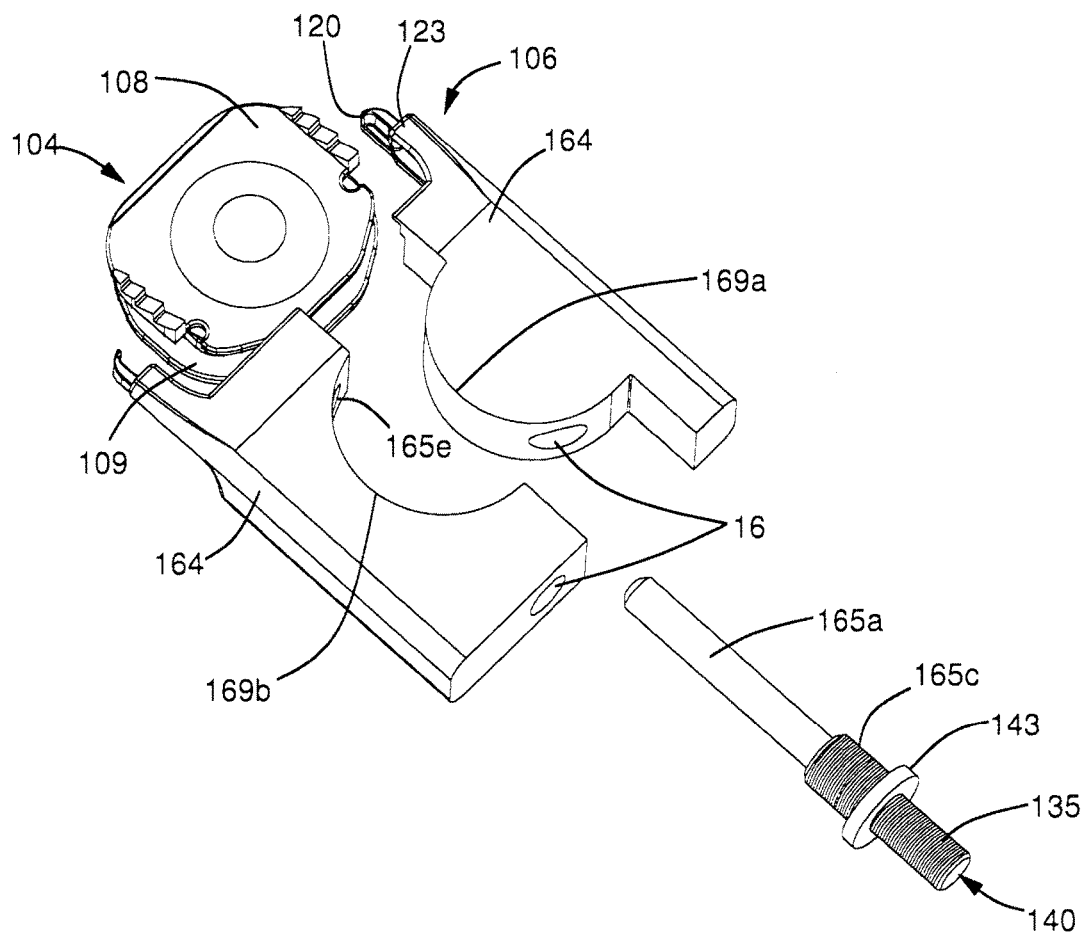
FIGS. 21A and 21B depict perspective views of, respectively, an embodiment of a disassembled prosthesis insertion assembly and an embodiment of an insertion adapter.
Figure 21B:
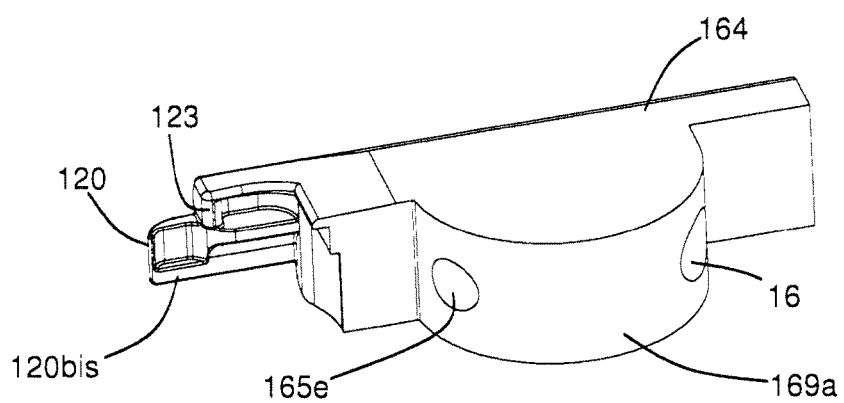

In some embodiments, an example of which is depicted in FIG. 20A, the two parts (164) of the adapter's (106) body cooperate together through curved surfaces: one part has a portion (169a) comprising a convex surface and the other has a portion (169b) comprising a concave surface, complementary to the convex surface. Thus, a first one of the two parts (164) forms a female part (169b) and the second one (164) forms a male part (169a) having a portion fitting into the female part (169b). In the example shown on FIG. 19A, the adapter (106) is at least partially crossed by a duct (or channel) (165e), such as a drilling for example, performed at the level of the male (169a) and female (169b) portions of the two parts of the body. Thus, a pin (165a) inserted in this duct (165e) enables assembling and maintaining together the two parts (164) of the adapter's body. In these embodiments, the duct (165e) and the pin (165a) are oriented along the longitudinal axis of the adapter (106). As particularly visible on FIGS. 20B and 20C, a threading (165c) on at least a portion of the pin (165a) can cooperate with a threading in the duct (165e). In this example, the pin also comprises a stop, for example such as a collar or skirt (143), for limiting the screwing of the pin. In some embodiments such as shown on FIGS. 20A to 20C, the male (169a) and female (169b) portions of the two parts (164) of the body are arranged so that a space (169c) is preserved between the two parts, at least at the end opposite the end holding the prosthesis. This space enables, when the pin (165a) is withdrawn from the duct (165e), that a pressure exerted on the lateral surfaces of the two parts (164), at the level of the end opposite the one holding the prosthesis, induces a rotation of the two part one in relation to the other, thanks to the complementarity of their respective curved surfaces and enables to free the prosthesis, in a manner similar to a clip. Furthermore, the duct (106e) can comprise an enlarged portion (16), so as to facilitate the insertion and withdrawal of the pin. The pin (165a) can, as shown on FIGS. 20(A to C), comprise a coupler (140) for the insertion tool (131). In this example shown, the coupler (140) comprises a flat (165d) intended to cooperate with a hole comprising a complementary shoulder, performed a one end of the actuator (136, FIG. 25B). Other configurations of the coupler (140) can of course be envisaged. For example, as particularly visible on FIG. 21A, the coupler (140) can consist of a stud or rod comprising a threading (135) on at least a portion and the pin (165a) can comprise a threading (165c) which screwing in the adapter is limited by a stop (143) such as a collar. In a particularly advantageous variant, the thread pitch of the threading (165c) of the pin (165a) and the thread pitch of the threading (135) of the coupler (140) are inversed, so that the screwing of the insertion tool (131) on the coupler (140) enables, when the tool stops on the collar (143), an unscrewing o the pin (165a) without requiring the surgeon to change the screw direction. FIG. 21B shows a detail of a part (164) of the adapter's body and, in particular, a shoulder (120bis) on dog (120) intended to hold the lower plate (109) of the prosthesis (104). This shoulder is arranged for efficiently maintaining the post (124) of the lower plate (109), which also comprises a complementary shoulder (12), as particularly visible on FIG. 22B. Similarly, FIG. 21B shows a dog (123) comprising a shoulder or a support surface for maintaining the upper plate (108).

Figure 23A:
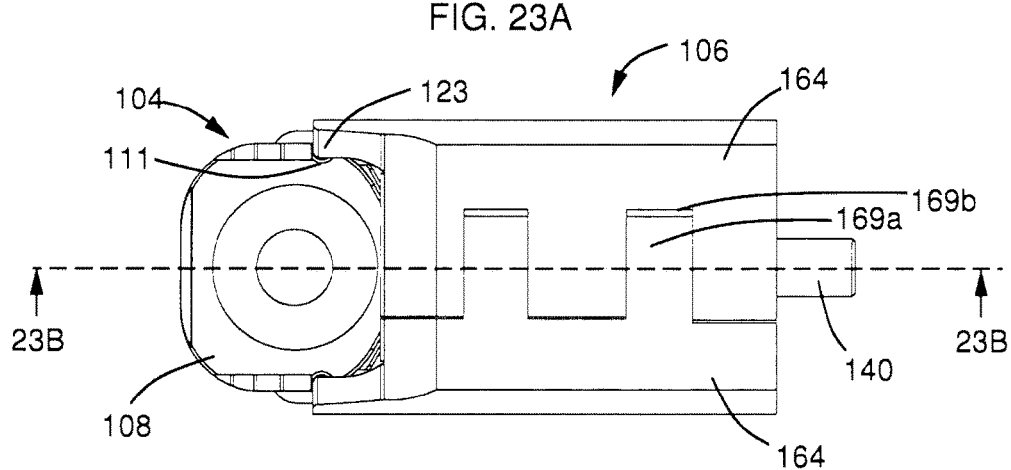
FIGS. 23A, 23B and 23C depict, respectively, an elevation view, a cross section view along cut plane (23B-23B) of FIG. 23A and a cross section view along cut plane (23C-23C) of FIG. 23B, of an embodiment of a prosthesis insertion assembly.
Figure 23B:
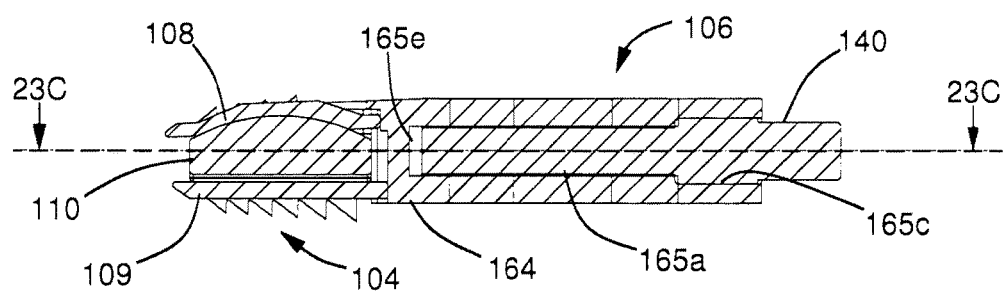
Figure 23C:
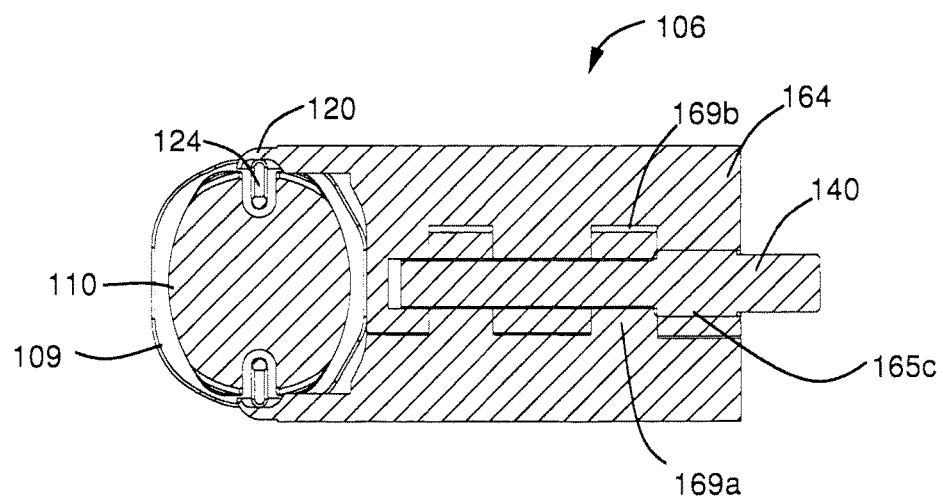
Figure 24A:
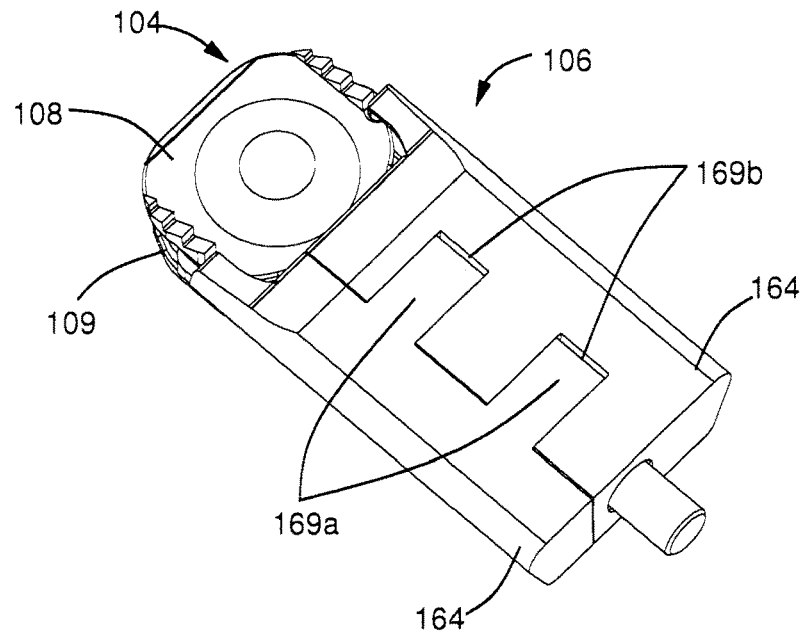
FIGS. 24A and 24B depict perspective views of an embodiment of a prosthesis insertion assembly, respectively assembled and disassembled.
Figure 24B:
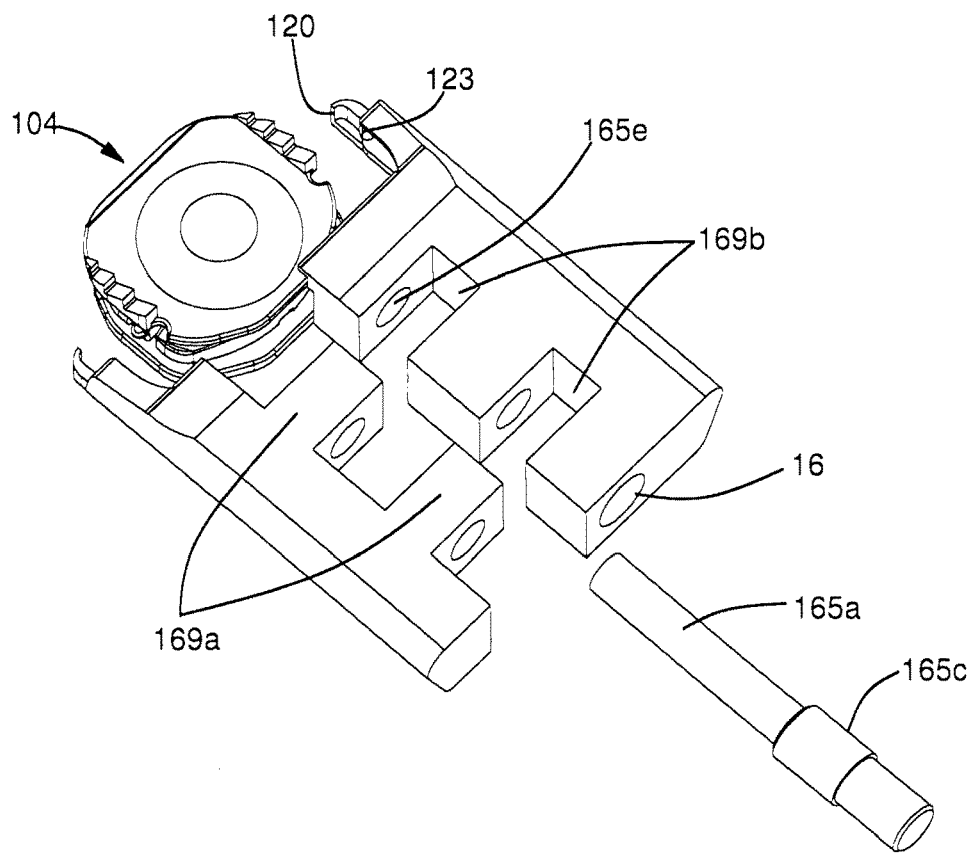

FIGS. 23A, 23B and 23C show another embodiment of the insertion adapter (106) split in two complementary parts (164). In this type of embodiments, a first one of the parts comprises at least one male portion (169a) and the second one comprises at least one female portion (169b) complementary to the male portion of the first part. In the example shown, two male portions having a substantially square or rectangular section cooperate with two female portions having a complementary shape. It will be understood, when appreciating the disclosure of this embodiment and the previous one, that the invention allows several embodiments of the male and female portions and that their number can vary. FIGS. 24A and 24 show the assembly/disassembly of the insertion adapter (106), by comparison, respectively, of an assembled view and a disassembled view of these embodiments. The assembly in this example is performed by bringing together the two parts (164) of the body and introducing the pin (165a) in the duct (165e). Similarly, the disassembly is performed by withdrawal of the pin and spreading of the two parts (164) apart.

Those of skill in the art, following appreciation of this disclosure, will recognize that many other structural configurations may be devised for the insertion adapter (106) to grasp the intervertebral disc prosthesis (104) and release the intervertebral this prosthesis (104) when inserted in an intervertebral disc space. Furthermore, the various embodiments and examples illustrated herein can be combined together, unless expressly mentioned herein or unless they are incompatible.

Some embodiments of the prosthesis insertion assembly (100) optionally may have a clip (126) that wraps around the assembled prosthesis (104) and holds the plates (108, 109) to the core (110). Retaining means such as the clip (126) augment the insertion adapter (106) in maintaining assembly of the prosthesis (104) during transport and/or during mounting, attaching, or assembling the insertion adapter (106) to or with the insertion tool body (130). Optionally, clip (126) may have one or more arrangement for removal (or removal means) to facilitate removal of the clip when the prosthesis insertion assembly (100) is assembled with, or mounted or attached to, an insertion tool body (130). These arrangements for removal can be such as tabs (127, 128) on the upper and lower surfaces (respectively) of the clip (126), as discussed further below.

In some preferred embodiments, the components of the intervertebral disc prosthesis (104) and the insertion adapter (106) may be sterilized using gamma radiation. Following sterilization, the components maybe packaged in primary sterile packaging (103a) to form a sterile pack (102), preferably with the components of the intervertebral disc prosthesis (104) and the insertion adapter (106) assembled as an insertion assembly (100), although packaging disassembled components of the intervertebral disc prosthesis (104) and the insertion adapter (106) is within the scope of this invention. In various preferred embodiments, the components of the intervertebral disc prosthesis (104) and the insertion adapter (106) that are packaged in primary sterile packaging (103a), whether assembled or disassembled, may be further packaged in a box or other container and enclosed in secondary sterile packaging (103b) to form a sterile pack (102). The sterile packaging (103a, 103b) may comprise bubble packaging, blister packaging, shrink wrapping, or other packaging configuration known to be suitable for maintaining the sterility of a medical implant. Sterile packaging (103a, 103b) in some embodiments preferably may have an oxygen absorbing packet, for example to reduce the potential for oxidative degradation of a polyethylene core (110) or other components. In preferred embodiments, the sterile pack (102) preferably may be made ready for delivery or transport to a sterile field of a surgical suite, directly or through a distributor.

Sterile packs (102) of insertion assemblies (100) preferably bear identifying information. For example, various embodiments optionally have a package label (198) with identifying information (180). The identifying information may include a use-before-date, the lot number and reference or serial number for the insertion assembly (100) or its components, a sterilization control label, and/or size and configuration information for the plates (108, 109) and the core (110). Preferably, the packaging label allows complete traceability of insertion assembly (100) from initial manufacturing through final implantation and service in a particular patient. In some embodiments, the sterile pack (102, 202) can comprise at least a transparent wall (107) enabling to see the insertion assembly (100, 101, 105) from outside the pack (102, 202).

Various embodiments described herein provide a surgical staff with an assortment or other inventory of pre-sterilized, pre-configured, and pre-assembled insertion assemblies (100). Optionally, a packaged intervertebral disc prosthesis insertion assembly may be provided with the intervertebral disc prosthesis (104) disassembled, along with an insertion adapter (106) preconfigured for use with the intervertebral disc prosthesis (104) following its assembly. In such embodiments, the components of the intervertebral disc prosthesis (104) typically would be assembled with the insertion adapter (106) in the sterile field to form an insertion assembly (100).

During a surgical procedure in various embodiments, the surgeon determines the appropriate dimensions and configurations of prosthesis (104). Measurements of the intervertebral disc space may, for example, be used in such a determination. Preferably, the surgical team may obtain the appropriate prosthesis insertion assembly (100) within the sterile field of the surgical suite from an inventory of prosthesis insertion assemblies (100).

In various disclosed embodiments such as shown in FIG. 4, whether providing the intervertebral disc prosthesis (104) assembled or disassembled, the prosthesis insertion assembly (100) may be configured for use with a detachable or demountable tool body (130), which may be used during the surgical procedure to implant the prosthesis (104) in the intervertebral disc space. The prosthesis insertion assembly (100) and the insertion tool body (130) preferably may be arranged or assembled for use, for example by attaching or mounting the prosthesis insertion assembly (100) to an insertion tool body (130), within the sterile field of a surgical suite.

Figure 5A:
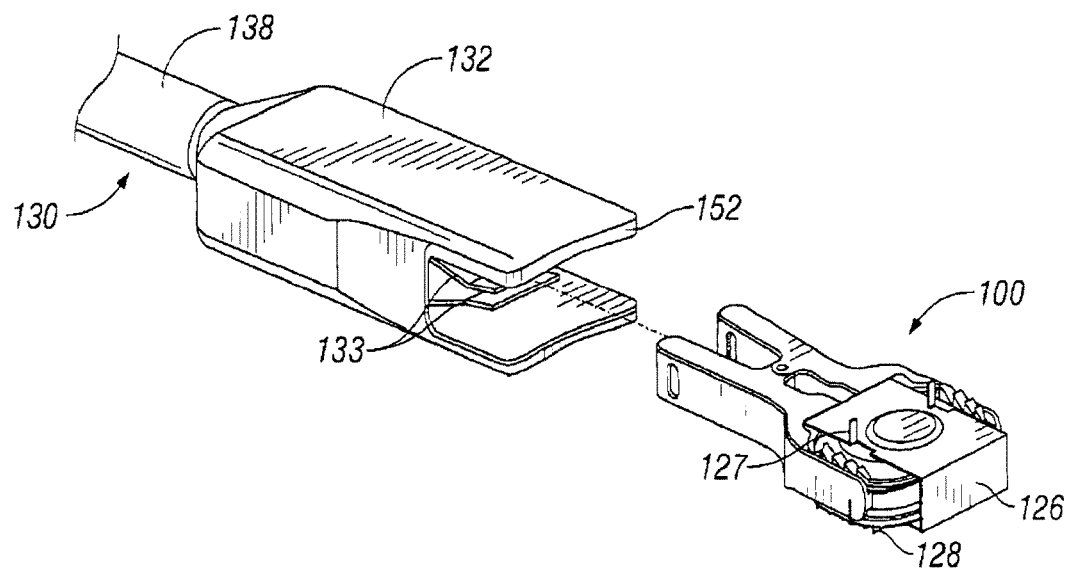
FIGS. 5A and 5b depict components of an embodiment of an insertion tool body and a prosthesis insertion assembly.
Figure 5B:
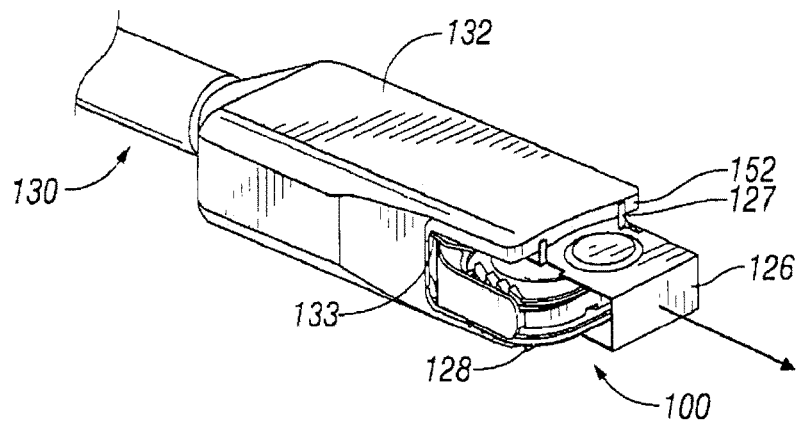

After removal from the sterile pack (102), the insertion assembly (100) and a detachable or demountable insertion tool body (130) are assembled. For the embodiments shown in FIGS. 5A and 5B, the prosthesis insertion assembly (100) may be lined up with a support (132), such as the illustrated housing for example, arranged to receive and support the prosthesis insertion assembly (100) during the implantation procedure. Preferably, the insertion tool body (130) may be adapted for use with all, or at least a wide assortment, of the various dimensions and configurations of intervertebral disc prostheses (104) available. There may be a wide variance in the heights of the various prostheses (104) in some embodiments of intervertebral disc prosthesis delivery and insertion systems. The support (132) optionally may be equipped with one or more retainers, for example the tongues (133) illustrated, to retain the prosthesis components in assembly. Other embodiments that deploy such retainers may use structures such as clips, pawls, springs, or other biasing components. Retainers such as tongues (133) may help center and support a wide variety of prosthesis dimensions and configurations with respect to support (132).

After appreciating the present disclosure, those of skill in the art will readily recognize numerous alternative means of mounting, coupling, assembling, attaching, or otherwise engaging a prosthesis insertion assembly (100) and an insertion tool body (130). For example, the insertion tool body (130) may be equipped with an actuator (136), such as a rod, shaft, cable, or other transmission or control structure, for example as illustrated in FIGS. 6A, 6B, and 6C. The actuator (136) in various embodiments may have engagement means, for example the illustrated threaded end (134) of the rod (136), to engage or connect with a coupler (140), for example the threaded hole illustrated in FIG. 3, of the insertion adapter (106). Once so engaged, the rod (136) may hold and push the insertion adapter (106) during the implantation procedure. The prosthesis insertion assembly (100) optionally may be attached or mounted to the insertion tool body (130) by engagement of the threaded end (134) with threaded hole (140). The insertion assembly (100) may be disposed by hand at least partially within support (132), at least to the point where the insertion assembly (100) engages the threaded end (134). The insertion assembly (100) may be further disposed by hand fully within support (132), causing the threaded end (134) to recess into the member (138) of the insertion tool body (130). At this point, the threaded end (134) may be rotated in threaded hole (140) until appropriate engagement of the threads is achieved and the prosthesis insertion assembly (100) is firmly retained in support (132). Alternatively, the threaded end (134) may, upon initial engagement with threaded hole (140), be rotated in threaded hole (140) until the prosthesis insertion assembly (100) is drawn fully within and retained in support (132). Regardless of how the prosthesis insertion assembly (100) is disposed into support (132), tabs (127, 128) on the respective upper and lower surfaces clip (126) may be configured to contact leading edges (152) of support (132), respectively, well before the insertion assembly (100) is seated in the insertion assembly (100), causing the clip (126) to detach from the prosthesis (104) as the insertion assembly (100) is further moved into support (132), for example as depicted in FIG. 5.

Figure 25A:
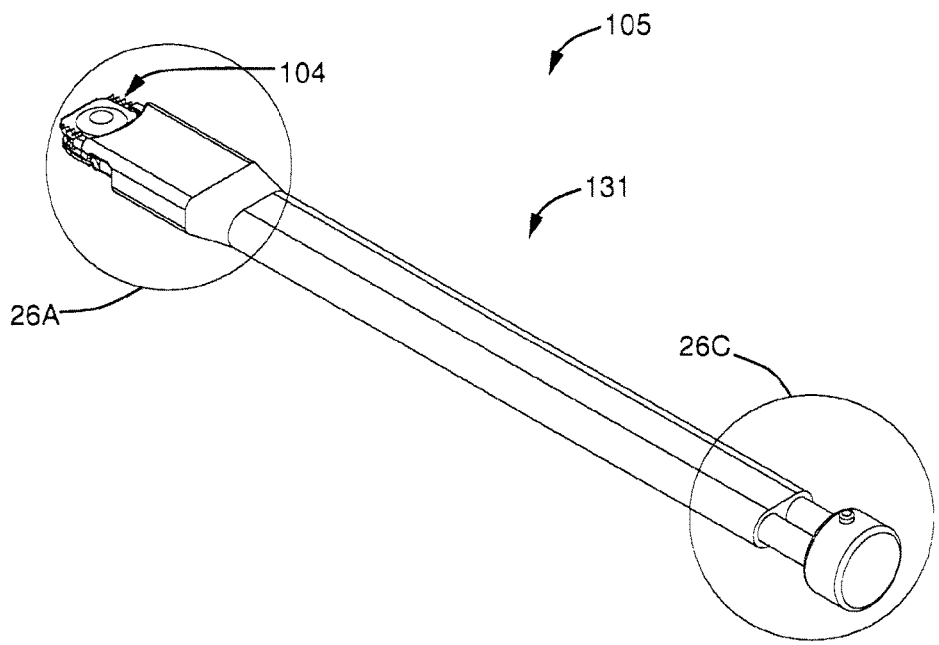
FIGS. 25A and 25B depict perspective views of an embodiment of a prosthesis insertion assembly, respectively assembled and disassembled.
Figure 25B:
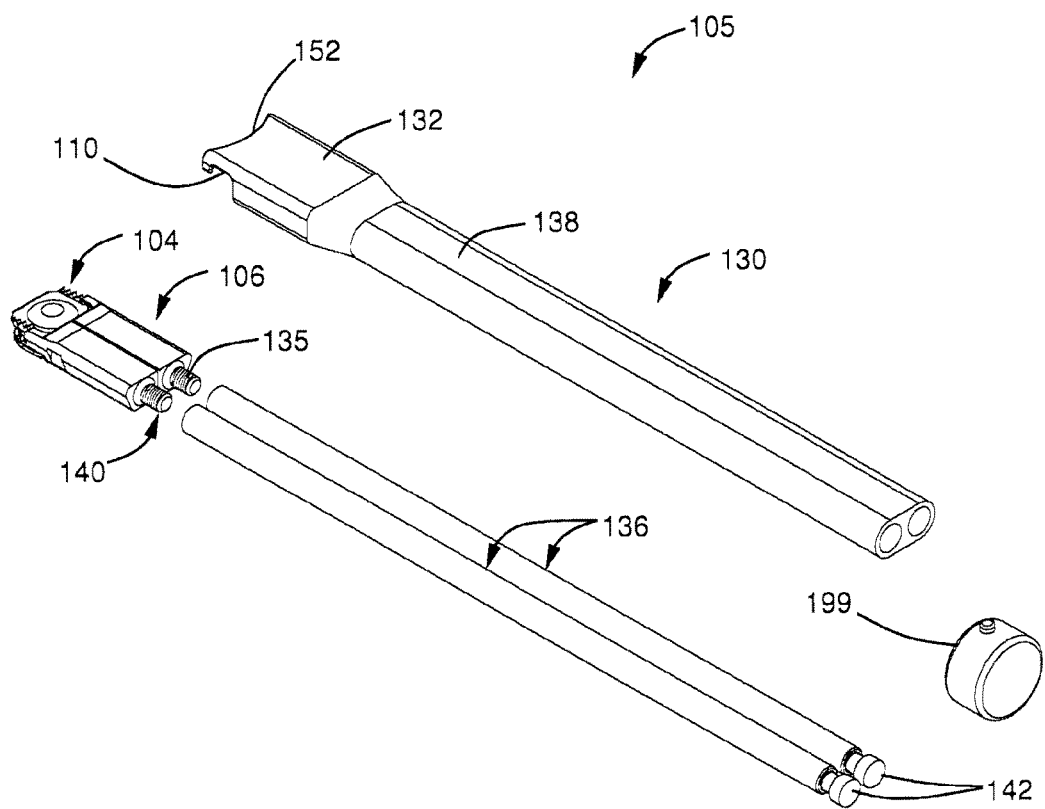
Figure 26A:
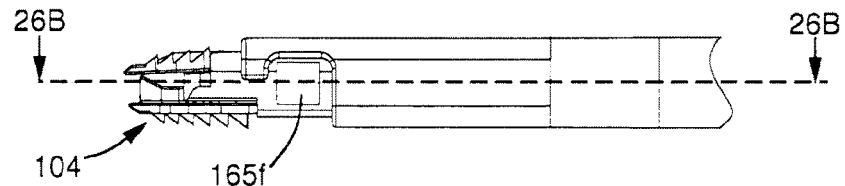
FIGS. 26A and 26B depict, respectively, a side view of a detail of the part of the prosthesis insertion assembly indicated by the reference 26A on FIG. 25A and a cross section view along cut plane (26B-26B) of the prosthesis insertion assembly of FIG. 26A, FIGS. 26C and 26D depicting, respectively, a side view of a detail of the part of the prosthesis insertion assembly indicated by reference 26C of FIG. 25A and a cross section view along cut plane (26D-26D) of the prosthesis insertion assembly of FIG. 26B.
Figure 26B:
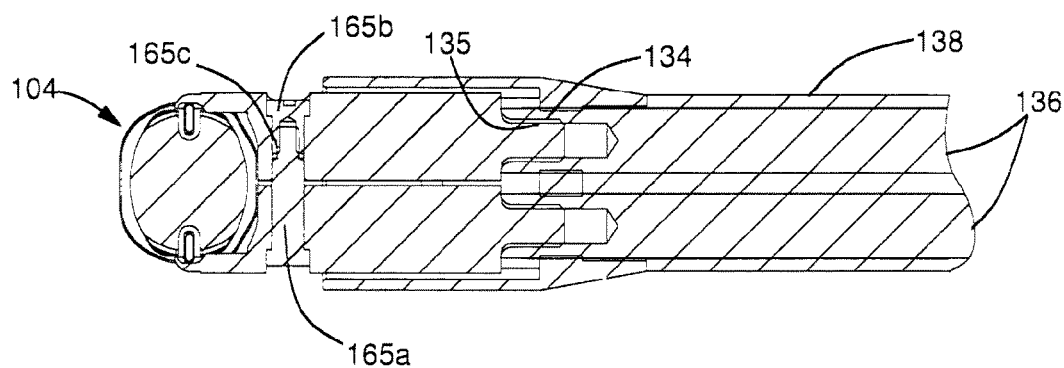
Figure 26C:
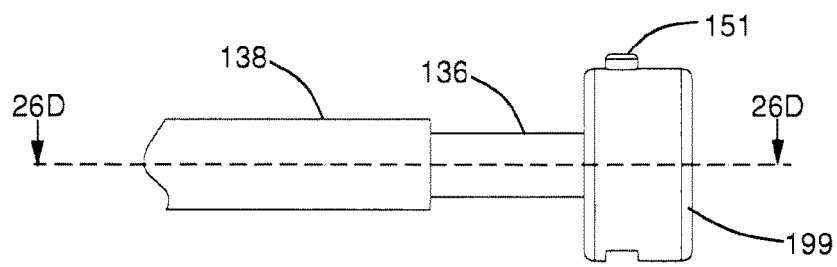
Figure 26D:
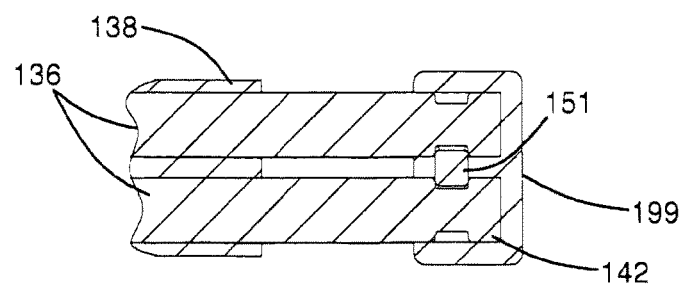

FIG. 25A shows a perspective view of an example of some embodiments of the insertion tool (131) maintaining insertion adapter (106) which body is split in two parts (164), for example such as shown on one of FIGS. 18 to 24, surrounding (holding) a prosthesis (104). The assembly formed by the prosthesis (104) held by the adapter (106) held by the insertion tool (131) can form an insertion assembly according to some embodiments of the present invention. In the embodiments of the insertion tool (131) corresponding to FIGS. 25 and 26, which are particularly suited for the embodiments of the adapter (106) of FIGS. 18 to 24, the actuating device (136) can comprise one or several rods having an end comprising a coupler (134) (such as a threaded hole for example) cooperating with the coupler(s) (140) of the adapter (such as at least one threaded rod in this example) for holding the prosthesis and having another end manipulated by the surgeon, for example thanks to a control device (142) such as a knob enabling the screwing of the actuating device (136) on the coupler of the adapter. In the embodiments shown, the actuating device(s) (136) is(are) arranged within a body (130) of the insertion tool comprising a member (138) which can be manipulated, such as an armature or a rigid envelope in which the actuator(s) (136) is(are) mounted free in rotation and in translation, so that actuating of the knob (142) allows to fix the adapter (106) on the insertion tool (131) (and reciprocally). The insertion tool (131) also comprises a support (132) comprising a housing with shape and dimensions arranged for receiving the insertion adapter (106) and comprising an edge (152) forming a stop intended to be placed in contact with at least one vertebra. It will be noted that, in these embodiments, the support (132) of the tool is not indispensable and that the edge (152) is useful for its role in indicating the position of the prosthesis in relation to the edges of the vertebrae. Thus, in some embodiments, the support (132) can be of a type which doesn't surround the adapter or can even be absent, the insertion tool (131) then comprising eventually a stop prolonging the member (138) for forming an edge (152) intended to be brought into contact with edges of the vertebrae. As shown on FIG. 25B, in some embodiments, the support (132) of the insertion tool (131) comprise, on at least one of its lateral surfaces, at least one recess (110) leaving a free access to at least lateral faces of the insertion adapter (106). Thus, as particularly visible on FIG. 26B, these recesses (110) enable accessing the swivel (165b) and/or the pin (165a) of an adapter (106) of a type such as shown on FIG. 18A for example, so that the pin can be withdrawn once the adapter is maintained by the insertion tool and before the insertion of the prosthesis (104) between vertebrae. Thus, once the prosthesis inserted between vertebrae, the adapter (106) can be easily disassembled when the insertion tool (131) is uncoupled from the adapter, while the unscrewing of the pin would have been tedious at this stage. In other embodiments, these recesses are not necessary because the pin (165a) is oriented along the longitudinal axis of the adapter (106) and can be withdrawn after the insertion of the prosthesis (104) between vertebrae. For example, in the embodiments having a pin (165a) screws in the adapter (106) by a threading (165c) inversed in relation to the threading (135) on which the actuating device (136) is screwed, the screwing of the actuating device induces the withdrawal of the pin and facilitate the release of the prosthesis by the adapter. In some embodiments, the insertion tool (131) also comprises a cap (199) mounted on an end of the actuator (136) comprising the control device (142) (or knob), so as to enable the surgeon to push on the assembly (105) and eventually strike on it (for example thanks to a tool) for inserting the prosthesis between vertebrae. As visible on FIGS. 26C and 26D, this cap (199) can comprise a ball or screw (151) enabling its fixation on one end of the actuator (136). As explained hereafter for other embodiments, in some embodiments similar to those shown on FIGS. 25 and 26, the insertion tool (131) can comprise at least one adjustable stop (144) for controlling the insertion of the prosthesis (104) inside the intervertebral space and/or a scale for indicating the position of the prosthesis (104) and/or of the adapter (106) with respect to the insertion tool (131) and/or to the vertebrae, for example thanks to the stop (152).

As shown in FIGS. 6A, 6B, and 6C, for some embodiments the actuator (136) may transit the member (138), which for example may be configured as a frame or shaft as illustrated. The actuator (136) may be equipped with a control at the end the insertion tool body (130) opposite the support (132), such as the knob (142) or a lever, button, or other control structure. In various embodiments, the control (142) may control both the delivery of the insertion adapter (106) and the prosthesis (104) to the intervertebral disc space from the support (132) as well as the release of the insertion adapter (106) from the insertion tool body (130) following such delivery, but separate controls may be provided for each function, and optionally may be provided for other functions. For insertion of the prosthesis (104) in various embodiments, the rod (136) may slide in the member (138) of the insertion tool body (130) toward the support (132) (the insertion direction), thus moving the insertion assembly (100) into the intervertebral disc space. With the insertion assembly (100) moved into the intervertebral disc space, threaded end (134) of rod (136) may be decoupled from the coupler of the insertion adapter (106) and the insertion tool body (130) moved away.

Various embodiments of the insertion tool body (130) may preferably be configured with an adjustable insertion stop to control the distance of the insertion of the intervertebral prosthesis (104) within the intervertebral disc space. FIGS. 6A, 6B, and 6C depict an exemplary adjustable stop configuration. In FIG. 6A, the prosthesis insertion assembly (100) is fully disposed in and firmly retained by support (132), with the threaded end (134) being substantially or fully engaged with threaded hole (140). A scale (147) may be disposed on a planar recess disposed on a shaft or stud (141) integral with or attached to the control knob (142). The scale (147) may be graduated in appropriate units of length and may include a zero mark (148). Tangs (164) and threaded hole (140) of insertion adapter (106) may be dimensioned and configured to accommodate further rotation of threaded end (134) in the threaded hole (140) in the position illustrated by FIG. 6A. Knob (142) may can be adjusted in handle (139) to position the zero mark (147) at an appropriate indicator, such as the end of handle (139) or other form of reference, for example as illustrated in FIG. 6B, which indexes knob (142), shaft or stud (141), rod (136), and the prosthesis insertion assembly (100) in the fully mounted position in support (132).

For various embodiments, when the zero mark (148) is set to the indicator with the prosthesis insertion assembly (100) in the fully mounted position in the support (132), for example as depicted in FIG. 6B, the scale (147) will indicate the distance that the prosthesis insertion assembly (100) has been extended from the support (132) by movement of the rod (136) within member (138) of insertion tool body (130). During the insertion of the intervertebral disc prosthesis (104), the leading edges (152) of the support (132) may be held firmly against respective vertebrae (150) defining the disc space receiving the prosthesis (104), as illustrated for example in FIGS. 8 and 10. Accordingly, the scale (147) can be used to indicate the distance of insertion of the prosthesis (104) within the intervertebral disc space.

Various embodiments may deploy an adjustable stop, for example a threaded nut (144) adjustable along threads (137) of the shaft or stud (141). The adjustable stop (144) may be used to control the distance of insertion of the prosthesis (104) within the intervertebral disc space. In various embodiments, for example, sliding of the rod (136) in the insertion direction will be stopped when the adjustable stop (144) abuts the end of handle (139). A stop lock may be used to maintain the setting of the stop (144), for example by use of a lock nut (146) as illustrated, or by other known locking structures. Preferably, the stop (144) will be adjusted in accordance with the size of the intervertebral disc space, typically measured and analyzed before the insertion stage of the surgical procedure as discussed elsewhere in this disclosure. FIG. 6C depicts an insertion assembly (100) extended from support (132) by a distance controlled by stop (144) abutting handle (139).

Figure 7:
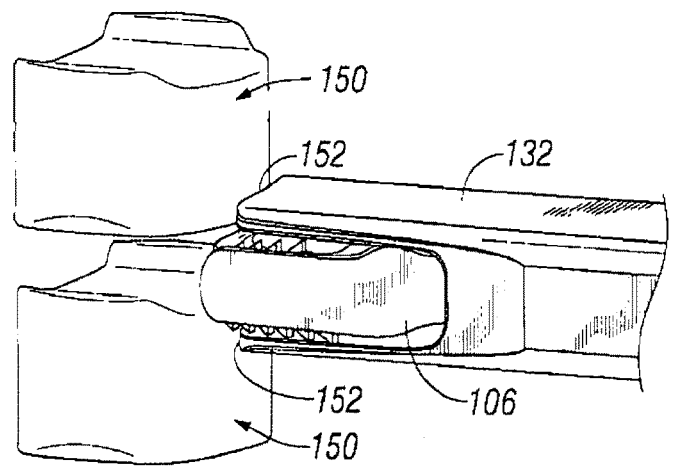
FIG. 7 depicts an embodiment of a prosthesis insertion assembly and a support of an insertion tool body.
Figure 8:
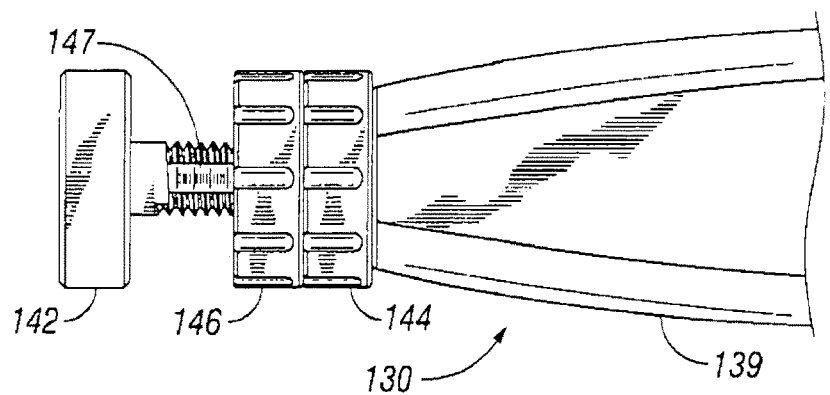
FIG. 8 depicts components and a portion of an embodiment of an insertion tool body.
Figure 9:
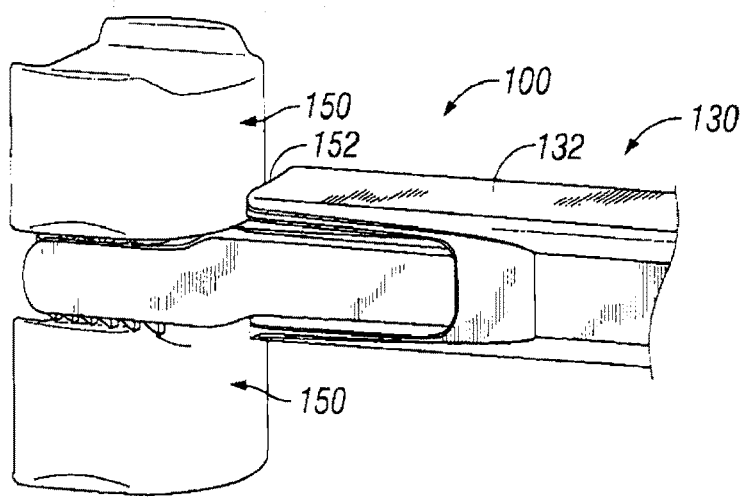
FIG. 9 depicts an embodiment of a prosthesis insertion assembly and a support of an insertion tool body.
Figure 10:
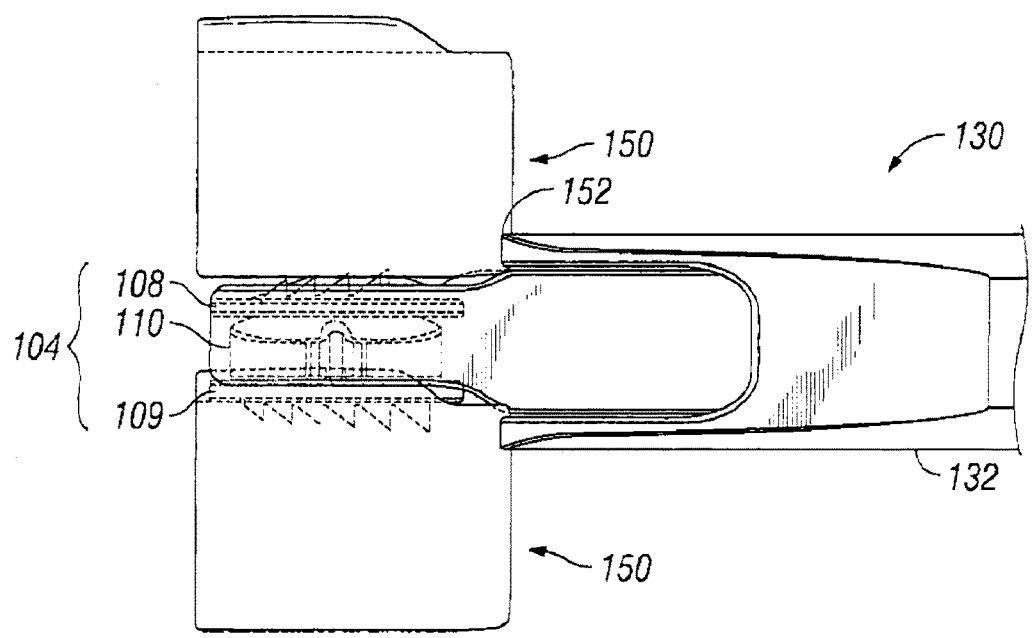
FIG. 10 depicts an embodiment of a prosthesis insertion assembly and a support of an insertion tool body.

FIG. 7 illustrates the commencement of the insertion stage of an embodiment of a surgical procedure. The insertion tool (130) and the prosthesis insertion assembly (100) may be configured and adjusted in accordance with the discussion above. The insertion tool (130) and the insertion assembly (100) may be located in the desired prosthesis insertion axis and located to place the leading edges (152) of the support (132) in contact with the respective vertebrae (150) defining the intervertebral disc space receiving the prosthesis (104). In various embodiments, the surgeon may apply force to the knob (142) by pressing it or striking it with a soft mallet or by hand. Force may be applied until the stop (144) abuts the end of the handle (139), as shown in FIG. 8. When the stop (144) abuts the end of the handle (139), the end (134) of the rod (136) will have pushed the insertion adapter (106) into position where the prosthesis (104) is properly positioned in the intervertebral disc space between the vertebrae (150). FIGS. 9 and 10 provide a representative illustration of the final positioning at this stage.

Figure 11:
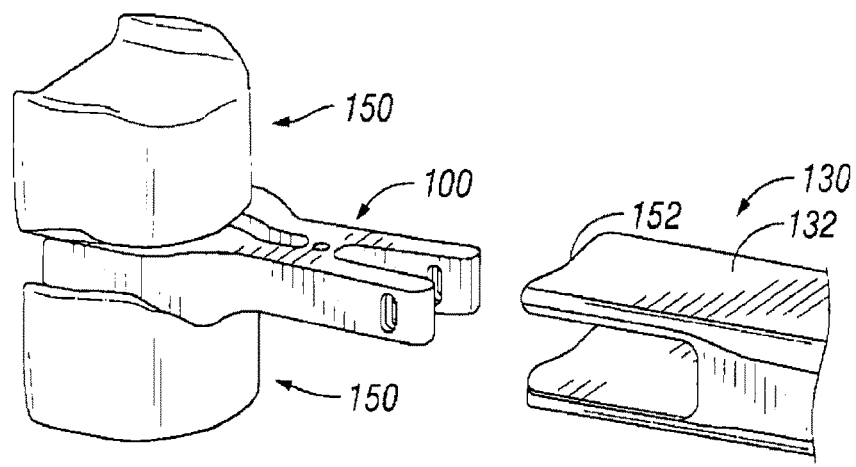
FIG. 11 depicts an embodiment of a prosthesis insertion assembly and a support of an insertion tool body.
Figure 12:
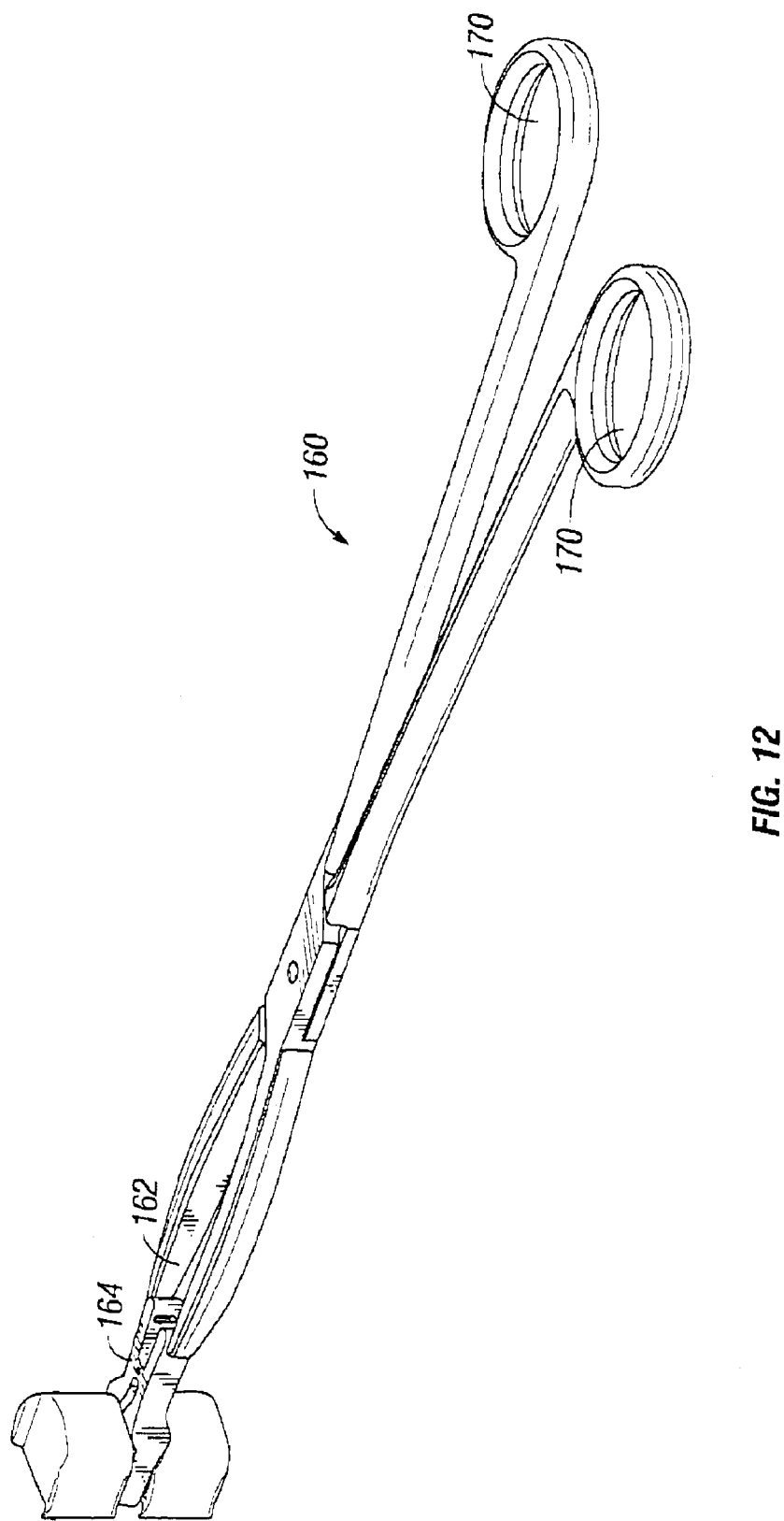
FIG. 12 depicts an embodiment of a removal tool.
Figure 13:
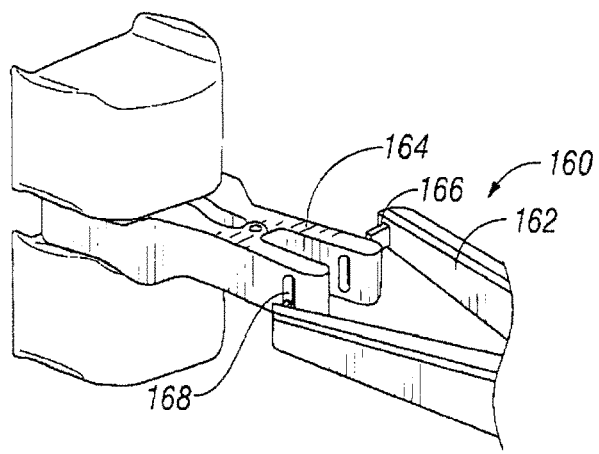
FIG. 13 depicts an embodiment of a prosthesis insertion assembly and a removal tool.
Figure 14:
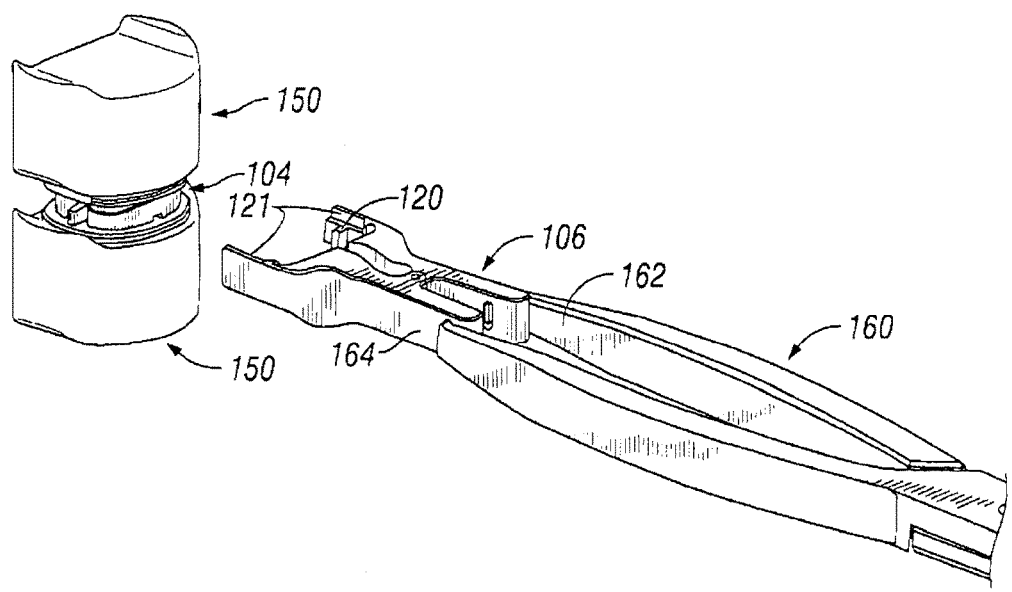
FIG. 14 depicts an embodiment of an intervertebral disc prosthesis, an insertion adapter, and a removal tool.

For various embodiments, the insertion tool body (130) may be detached or demounted from the insertion assembly (100) by rotating the knob (142) counter-clockwise until the threaded end (134) releases from the threaded hole (140). FIG. 11 shows the insertion tool body (130) as it is being withdrawn, leaving only the insertion assembly (100) in the opening between the vertebrae (150). A removal tool (160), for example as shown in FIG. 12, may be used to separate the insertion adapter (106) from the prosthesis 104, leaving the prosthesis (104) implanted in the intervertebral disc space. FIG. 13 shows the removal tool (160) approaching the insertion adapter (106). Tool ends (162) of the removal tool (160) may be positioned along the tangs (164) of the insertion adapter (106) in such a way that pins (166) enter slots (168) disposed in the tangs (164). Other embodiments may include a single hole in each tang (164), multiple smaller holes or slots, or any of many other means for the removal tool (160) to attach with, connect to, or latch on the tangs (164) of the insertion adapter (106). Actuating a removal tool (160) by squeezing handles (170) of the removal tool (160) may pivot the tangs (164) of the insertion adapter (106) around the hinge pin (172), causing the jaws (121) to release the plates and the mounting dogs (120) to release their grip on the posts (124) and disengage from the recesses (122). In alternative embodiments of insertion adapter (106) comprising a flexible portion at which the tangs (164) articulate, squeezing the tangs (164) will cause the flexible body to flex, the tangs (164) to articulate, the jaws (121) to release the plates, and the mounting dogs (120) to release their grip on the posts (124) and disengage from the recesses (122). Once the insertion adapter (106) releases the prosthesis (104), the insertion adapter (106) may be removed, for example as shown in FIG. 14, leaving the prosthesis (104) properly positioned in the disc space between the two vertebrae (150).

Figure 15:
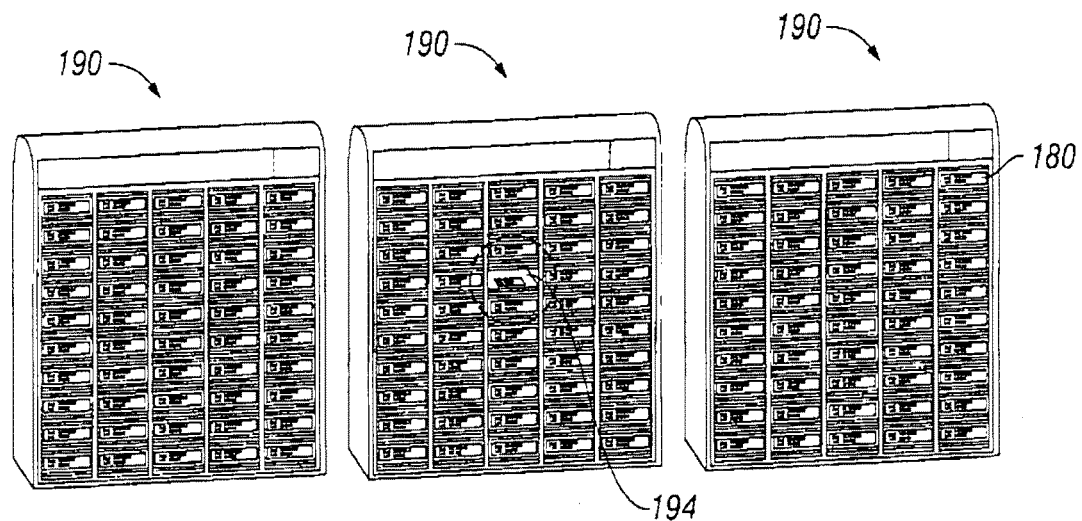
FIG. 15 depicts an embodiment of inventory storage space and a storage location.

Various embodiments of an intervertebral disc prosthesis delivery and insertion system also maybe provided. In a preferred embodiment, the sterile pack (102) inventory may be maintained in dedicated inventory storage space, for example racks (190) as illustrated in FIG. 15. Various embodiments may have prostheses each configured with a first plate having a size and configuration selected from a set of first size and configuration specifications, a second plate having a size and configuration selected from a set of second size and configuration specifications, and a core having a size and configuration selected from a set of third size and configuration specifications. The first plate, the second plate, and/or the core configuration optionally may specify a lordosis or kyphosis correction. In various embodiments, any of the sets of size and configuration specifications may contain only one element, in which case the particular component may be provided in only one size and configuration.

Preferably, the inventory will be organized by plate dimension, core height, and lordosis/kyphosis correction angle (if any), but other characteristics of the prostheses (104) may be used for an organizational scheme. Each rack (190), for example, may contain insertion assemblies (100) of various dimensions all having a particular lordosis/kyphosis correction angle, with the sterile packs (102) organized in the respective racks (190) in rows by the plate dimension and in columns by the core height of the packaged prostheses (104). Alternatively, any organization scheme using any combination of the set of first size and configuration specifications, the set of second size and configuration specifications, and/or the third size and configuration specifications may be used. Preferably, each storage location (194) corresponds to one of the selected combinations of first size and configuration specifications, second size and configuration specifications, and/or third size and configuration specifications.

As noted above, in various embodiments the sterile packs (102) of insertion assemblies (100) preferably bear identifying information. For example, various embodiments optionally have a package label (198, FIG. 16) with identifying information (180). The label (180) disposed on a sterile pack (102) preferably will indicate the enclosed prosthesis's plate dimension, core height, and lordosis/kyphosis correction angle (if any), along with the stock-keeping unit (SKU) designation of the sterile pack (102) and the other information discussed above, some or all of which preferably may be encoded in scannable code included on the label or other component of the packaging, for example a chip or transponder. Other information (180) optionally may be provided, for example further logistical management information such as inspection data, reorder points, lead times, etc., or information relevant to surgical techniques and equipment. Coding can be done with bar or other optical codes, magnetic stripes, radio-frequency identification, or other known techniques. The identifying information (180) on a sterile pack (102) preferably may be readable when insertion assembly (100) is stocked in the rack.

Figure 16:
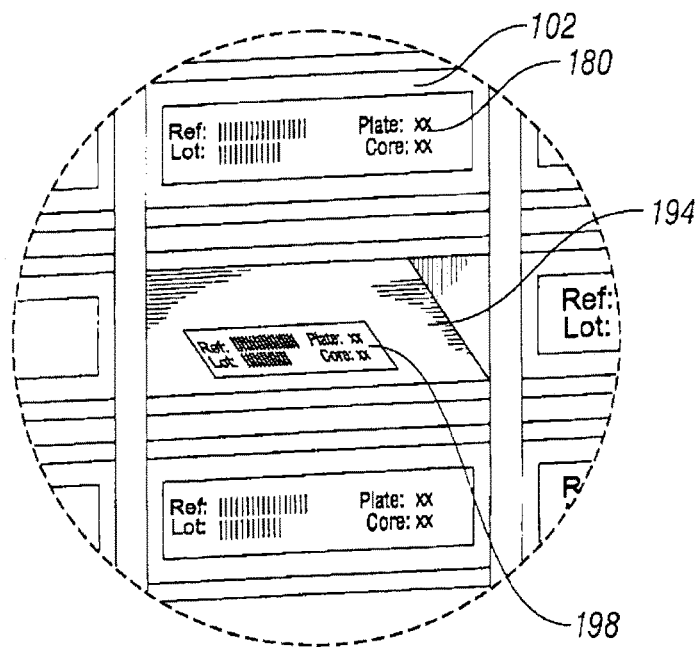
FIG. 16 depicts an embodiment of a storage location and configuration information.

The sterile pack (102) storage locations, for example bins (194) of the racks (190), optionally each may contain a label having identifying information for the sterile pack (102) that should be stocked in that bin (194), for example as depicted in FIG. 16. Other means of providing the information about the sterile pack (102) that should be stored in the bin (194), of course, may be use, for example magnetic stripes, radio-frequency identification, or other known techniques. Preferably, each bin label (194) or other form of identifying information may be readable when the respective bin (194) is empty. Thus, stock keeping may be simplified by providing sufficient information for re-ordering from routine observation of empty rack spaces, and acquisition of the correct assembly (100) during surgery may be simplified by the rack's organizational scheme. Stock keeping and insertion assembly (100) acquisition can be further enhanced by providing label- or other information-scanning equipment in the sterile field of the surgical suite, which will provide another level of verification of sterile pack (102) ordering and acquisition.

After appreciating this disclosure, those of skill in the art will recognize that other logistical management techniques advantageously can be applied to the intervertebral disc prosthesis delivery and insertion systems and methods disclosed herein.

Figure 17:
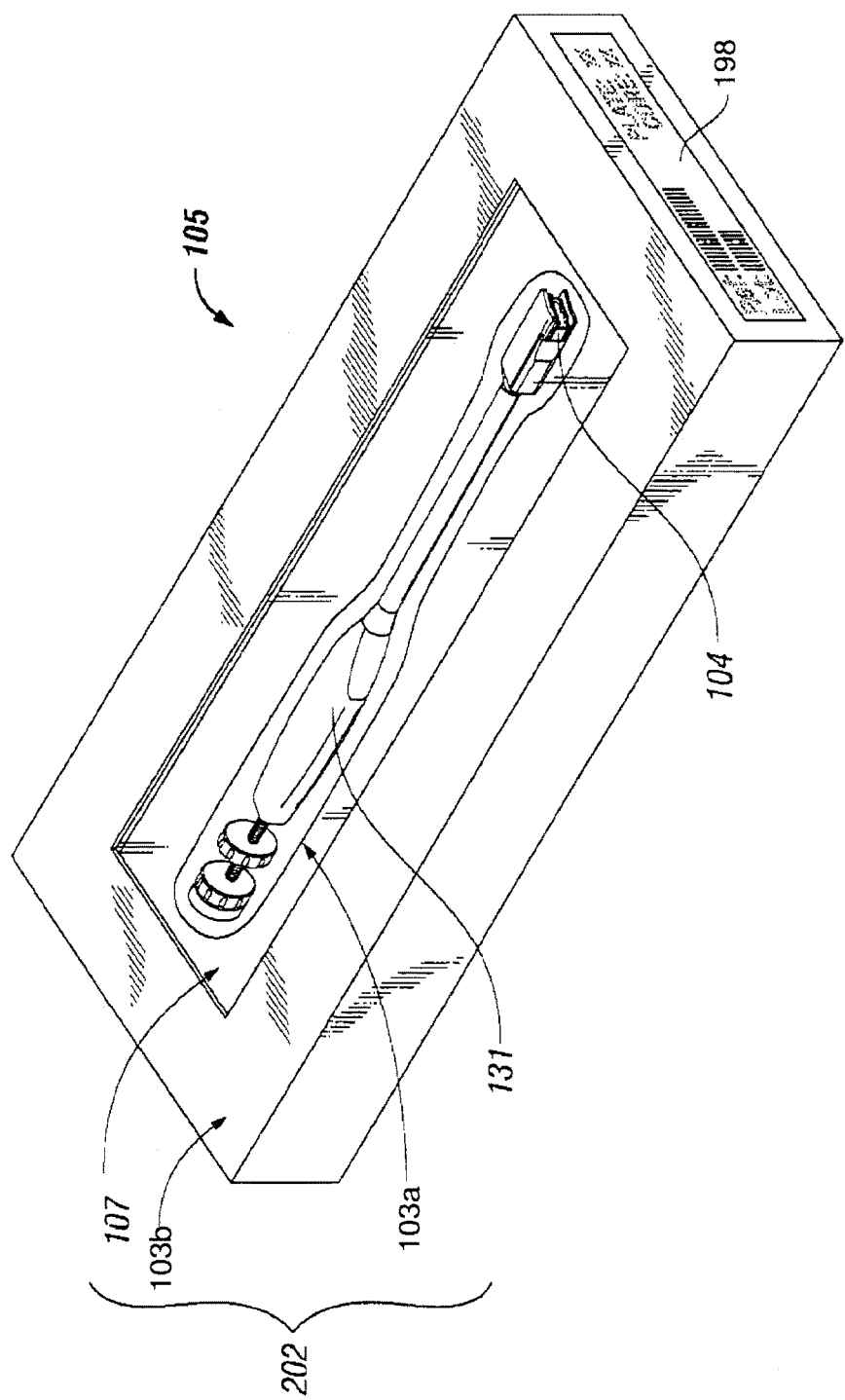
FIG. 17 depicts an embodiment of a sterile pack comprising a prosthesis insertion assembly.

Various features of embodiments of a packaged intervertebral disc prosthesis insertion assembly (101) comprising a sterile insertion adapter (106) and sterile components of n intervertebral disc prosthesis (104) are described above. Those of skill in the art will recognize after appreciating this disclosure that similar features may be provided in embodiments of a packaged intervertebral disc prosthesis insertion assembly (105) comprising a sterile insertion tool (131) and sterile components of an intervertebral disc prosthesis (104). For example, as shown in FIG. 17 the sterile insertion tool (131) and the sterile intervertebral disc prosthesis (104) may be assembled together and disposed in primary, or inner, sterile packaging (103a) and in secondary, or outer, sterile packaging (103b) to form a sterile pack (202). The components of the intervertebral disc prosthesis (104) in this embodiment maybe assembled with the sterile insertion tool (131) and provided to the sterile field of a surgical suite pre-configured and ready to use. The sterile insertion tool (131) optionally may have an insertion tool body (130) and a detachable insertion adapter (106), which may be packaged, assembled or disassembled. Alternatively, the sterile insertion tool (131) may have an insertion adapter (106) integral with an insertion tool body (130), or the sterile insertion tool (131) may have other structures devised to hold the intervertebral disc prosthesis (104) and/or deliver it to the intervertebral disc space. Various features of the insertion adapter (106) and/or the insertion tool body (130) discussed above, and/or the various components of the foregoing and other components discussed above, optionally may be included for the packaged intervertebral disc prosthesis insertion assembly (105). Various features the intervertebral disc prosthesis delivery and insertion systems discussed above, as well as features of other systems, optionally may also be used with a packaged intervertebral disc prosthesis insertion assembly (105) comprising a sterile insertion tool (131) and sterile components of an intervertebral disc prosthesis (104).

Those of skill in the art will recognize after appreciating this disclosure that the steps of the various methods, processes, and other techniques disclosed herein need not be performed in any particular order, unless otherwise expressly stated or logically necessary to satisfy expressly stated antecedent conditions. In addition, after appreciating this disclosure those skilled in the art will recognize that the invention may be embodied in a variety of different forms and that various changes, substitutions, and alterations can be made without departing from the spirit and scope of the invention. The described embodiments are illustrative only and are not restrictive, and the scope of the invention is defined solely by the following claims.

The invention claimed is:

1. An intervertebral disc prosthesis insertion assembly having a longitudinal axis extending from an insertion end of the intervertebral disc prosthesis insertion assembly to a tool-attachment end of the intervertebral disc prosthesis insertion assembly and comprising:
   an intervertebral disc prosthesis;
   a pin having a central axis and an insertion tool coupler; and
   an insertion adapter comprising
      a first arm comprising a first jaw disposed along the insertion end and a first tang disposed along the tool-attachment end, and
      a second arm comprising a second jaw disposed along the insertion end and a second tang disposed along the tool-attachment end;
   the intervertebral disc prosthesis insertion assembly having
      an assembled configuration in which the pin is inserted into the first arm and the second arm with the central axis extending in the direction of the longitudinal axis, the first jaw and the first tang disposed on a first side of the central axis, the second jaw and the second tang disposed on a second side of the central axis opposite the first side, and the intervertebral disc prosthesis retained between the first jaw and the second jaw by the insertion of the pin into the first arm and the second arm, and a released configuration in which the pin is outside the first arm and the second arm and the intervertebral disc prosthesis is released from the first jaw and the second jaw.

2. An intervertebral disc prosthesis insertion assembly according to claim 1 in which in the insertion adapter is separated along the longitudinal axis into the first arm and the second arm, with the first arm comprising a first protrusion placed and sized to fit within a first recess of the second arm with the intervertebral disc prosthesis insertion assembly arranged in the assembled configuration.

3. An intervertebral disc prosthesis insertion assembly according to claim 2 in which the first arm has a first channel, the second arm has a second channel, and the first channel and the second channel are arranged to form a collinear channel with the intervertebral disc prosthesis insertion assembly arranged in the assembled configuration.

4. An intervertebral disc prosthesis insertion assembly according to claim 3 in which the pin is disposable in the first channel and the second channel with the intervertebral disc prosthesis insertion assembly arranged in the assembled configuration.

5. An intervertebral disc prosthesis insertion assembly according to claim 4 in which the insertion tool coupler comprises threading disposed on an end of the pin.

6. An intervertebral disc prosthesis insertion assembly according to claim 5 in which the first protrusion comprises a convex surface having a first curvature and the first recess comprises a concave surface having second curvature that is complementary to the first curvature.

7. An intervertebral disc prosthesis insertion assembly according to claim 6 in which:
the first arm has a first jaw extension comprising a first dog sized to fit a first notch in a first plate of the prosthesis and a second dog sized to hold a first post on a second plate of the prosthesis;
the second arm has a second jaw extension comprising a third dog sized to fit a second notch in a first plate of the prosthesis and a fourth dog sized to hold a second post on a second plate of the prosthesis; and
the first jaw extension and the second jaw extension form a first gap in which the prosthesis is disposed with the intervertebral disc prosthesis insertion assembly arranged in the assembled configuration.

8. An intervertebral disc prosthesis insertion assembly according to claim 7 in which:
the first jaw comprises a first shoulder;
the second jaw comprises a second shoulder; and
the first shoulder and the second shoulders grip edges of the second plate with the intervertebral disc prosthesis insertion assembly arranged in the assembled configuration.

9. An intervertebral disc prosthesis insertion assembly according to claim 8 in which:
a second gap separates the first tang from the second tang with the intervertebral disc prosthesis insertion assembly arranged in the assembled configuration; and
with the intervertebral disc prosthesis insertion assembly in the released configuration, the first tang is disposed proximal to the second tang at a distance less than the second gap, the first arm is rotated along the convex surface and the concave surface relative to the second arm, and the first and second shoulders are not in contact with edges of the second plate.

10. An intervertebral disc prosthesis insertion assembly according to claim 3 in which the first protrusion is shaped as a rectangular cuboid and the first recess has generally planar walls sized and placed to accept the first protrusion with the intervertebral disc prosthesis insertion assembly arranged in the assembled configuration.

11. An intervertebral disc prosthesis insertion assembly according to claim 10 in which the first arm comprises a second protrusion, and the second arm comprises a second recess sized and placed to accept the second protrusion with the intervertebral disc prosthesis insertion assembly arranged in the assembled configuration.

12. An intervertebral disc prosthesis insertion assembly according to claim 11 in which the second protrusion is shaped as a rectangular cuboid and the second recess has generally planar walls.

13. An intervertebral disc prosthesis insertion assembly according to claim 3 in which the first channel extends through the first protrusion.

14. An intervertebral disc prosthesis insertion assembly according to claim 1, further comprising an insertion tool.

15. An intervertebral disc prosthesis insertion assembly according to claim 14, in which the insertion tool comprises a demountable insertion tool body releasably mountable to the coupler.

16. An intervertebral disc prosthesis insertion assembly implantable in a spine by a surgical operation, the insertion assembly comprising:
an intervertebral disc prosthesis; and
an insertion adapter having a longitudinal axis extending between an insertion end and an attachment end, the insertion adapter comprising plural separate body components having first and second configurations,
with the body components joined together in the first configuration by a pin oriented along the longitudinal axis and holding the body components juxtaposed and grasping the prosthesis with pressure applied by a jaw disposed on the insertion end of each of the body components, and with a coupler on an end of the pin extending outside the body components along the attachment end of the insertion adapter, and
with the body components disjoined apart in the second configuration.

17. The intervertebral disc prosthesis insertion assembly of claim 16 in which each of the body components comprises a first end, a second end, and a midsection disposed between the first and second ends, and in which the insertion adapter comprises an articulation of the body components formed by contact of portions of the midsections of each of the body components, with the jaws spaced further apart when the send ends are placed closer together.

18. The intervertebral disc prosthesis insertion assembly of claim 17 in which the articulation comprises a convex part of the midsection of one of the body components and concave part of the midsection of another one of the body components.

19. An intervertebral disc prosthesis insertion assembly comprising:
an intervertebral disc prosthesis and
an insertion adapter, the insertion adapter comprising a first jaw comprising a first duct, a second jaw comprising a second duct, and a pin disposable into and removable from the first duct and the second duct, the insertion adapter having a first arrangement in which
  the pin is disposed into the first duct and into the second duct with a tool coupler on an end of the pin extending outside the first duct and the second duct, and
  the first jaw and the second jaw are held together by the pin proximally such that the intervertebral disc prosthesis is securely grasped by the first jaw and the second jaw, and
a second arrangement in which the pin is removed from the first duct and the second duct, the first jaw and the second jaw are released from each other, and the intervertebral disc prosthesis is released from the insertion adapter.

20. The intervertebral disc prosthesis of claim 19 in which the pin is retained in the first duct by a threading when the insertion adapted is arranged in the first arrangement.

\* \* \* \* \*